(12) United States Patent
Wang et al.

(10) Patent No.: US 8,275,436 B2
(45) Date of Patent: Sep. 25, 2012

(54) METHOD AND APPARATUS FOR NON-INVASIVE FETAL OXIMETRY

(76) Inventors: Yixiang Wang, Fremont, CA (US); Wen Huang, Cupertino, CA (US)

(*) Notice: Subject to any disclaimer, the term of this patent is extended or adjusted under 35 U.S.C. 154(b) by 471 days.

(21) Appl. No.: 12/715,974

(22) Filed: Mar. 2, 2010

(65) Prior Publication Data

US 2011/0218413 A1    Sep. 8, 2011

(51) Int. Cl.
*A61B 5/00* (2006.01)
(52) U.S. Cl. .............................. 600/324; 600/338
(58) Field of Classification Search .............. 600/324, 600/338
See application file for complete search history.

(56) References Cited

U.S. PATENT DOCUMENTS

| | | | | |
|---|---|---|---|---|
| 7,047,055 | B2 * | 5/2006 | Boas et al. ................. | 600/338 |
| 7,515,948 | B1 * | 4/2009 | Balberg et al. ............. | 600/323 |
| 2010/0137727 | A1 * | 6/2010 | Sameni et al. ............. | 600/511 |

* cited by examiner

Primary Examiner — Clayton E Laballe
Assistant Examiner — Dennis Hancock

(74) Attorney, Agent, or Firm — Stephen E. Zweig

(57) ABSTRACT

Method and apparatus to non-invasively measure fetal blood oxygen saturation levels. Optical sensors capable of producing and detecting multiple wavelengths of tissue penetrating light are placed on the surface of the maternal abdomen, and the light beams directed to pass through at least a portion of the uterus containing the fetus. The fetal heart rate is monitored by Doppler ultrasound, and pure maternal optical signal related to maternal arterial blood flow are also measured. The optical sensors collect composite signals containing both maternal and fetal hemoglobin absorption spectral data and modulated by their respective pulsatile blood flows. The composite signals processed in the time domain and frequency domain, the pure maternal pulsatile optical signal used to extract the maternal contribution to the composite signal, and the fetal pulsatile signal is used to lock onto and extract the fetal contribution to the composite signal, and a fetal blood oxygen level deduced.

19 Claims, 18 Drawing Sheets

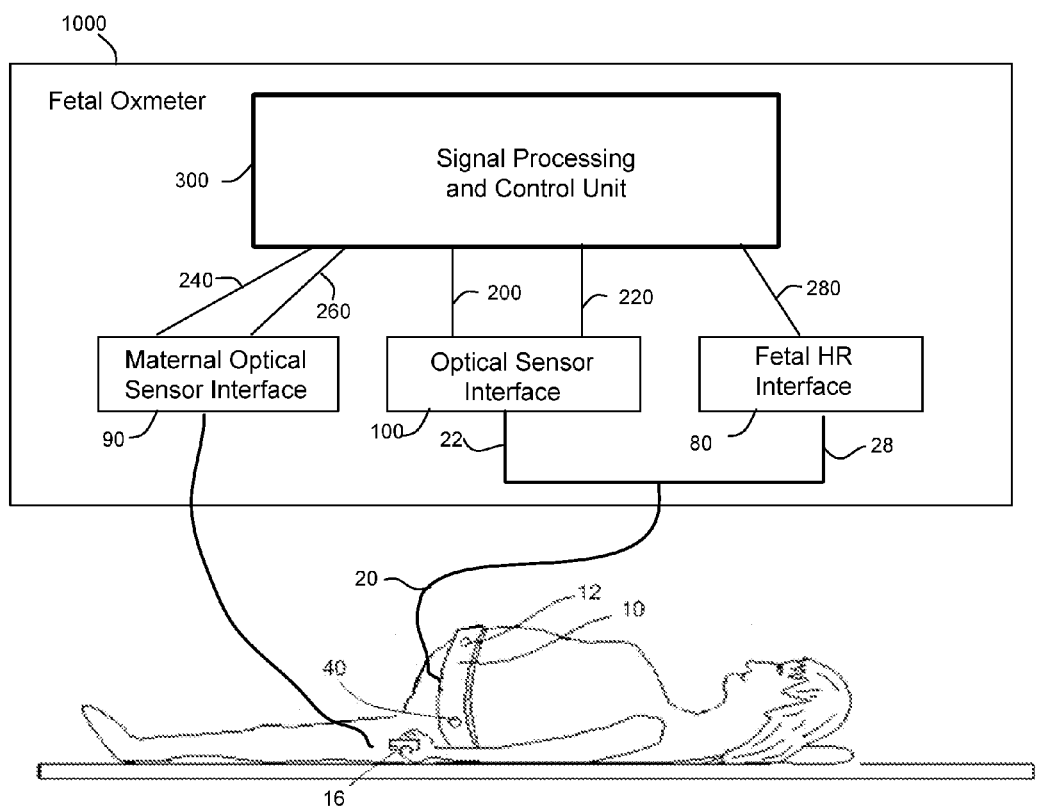

Figure 7

$$X_k = \sum_{n=0}^{N-1} x_n e^{-i2\pi k \frac{n}{N}} \qquad k = 0, \ldots, N-1.$$

Figure 7A $$X(z) = \mathcal{Z}[\{x_n\}_{n=0}^{\infty}] = \sum_{n=0}^{\infty} x_n z^{-n} = \sum_{n=0}^{\infty} x[n] z^{-n}$$

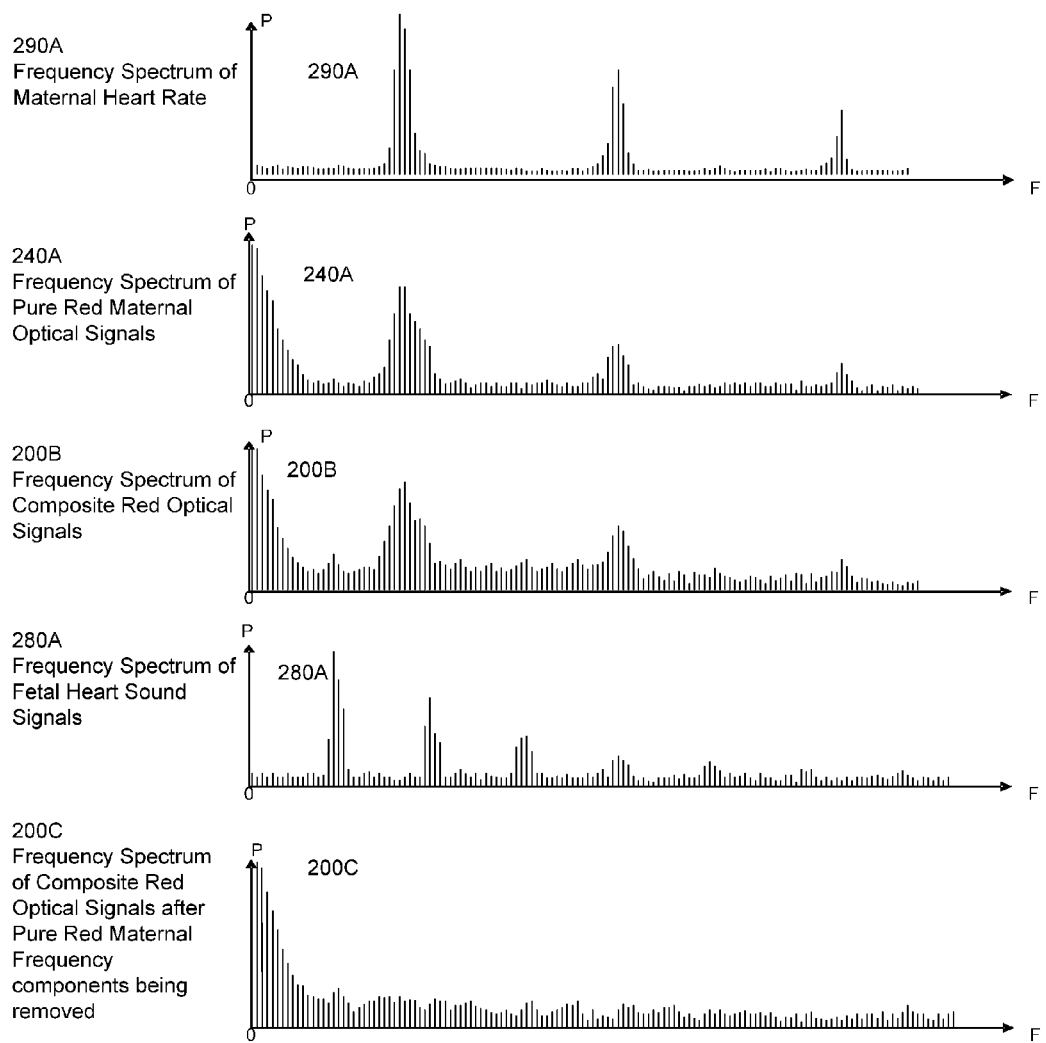

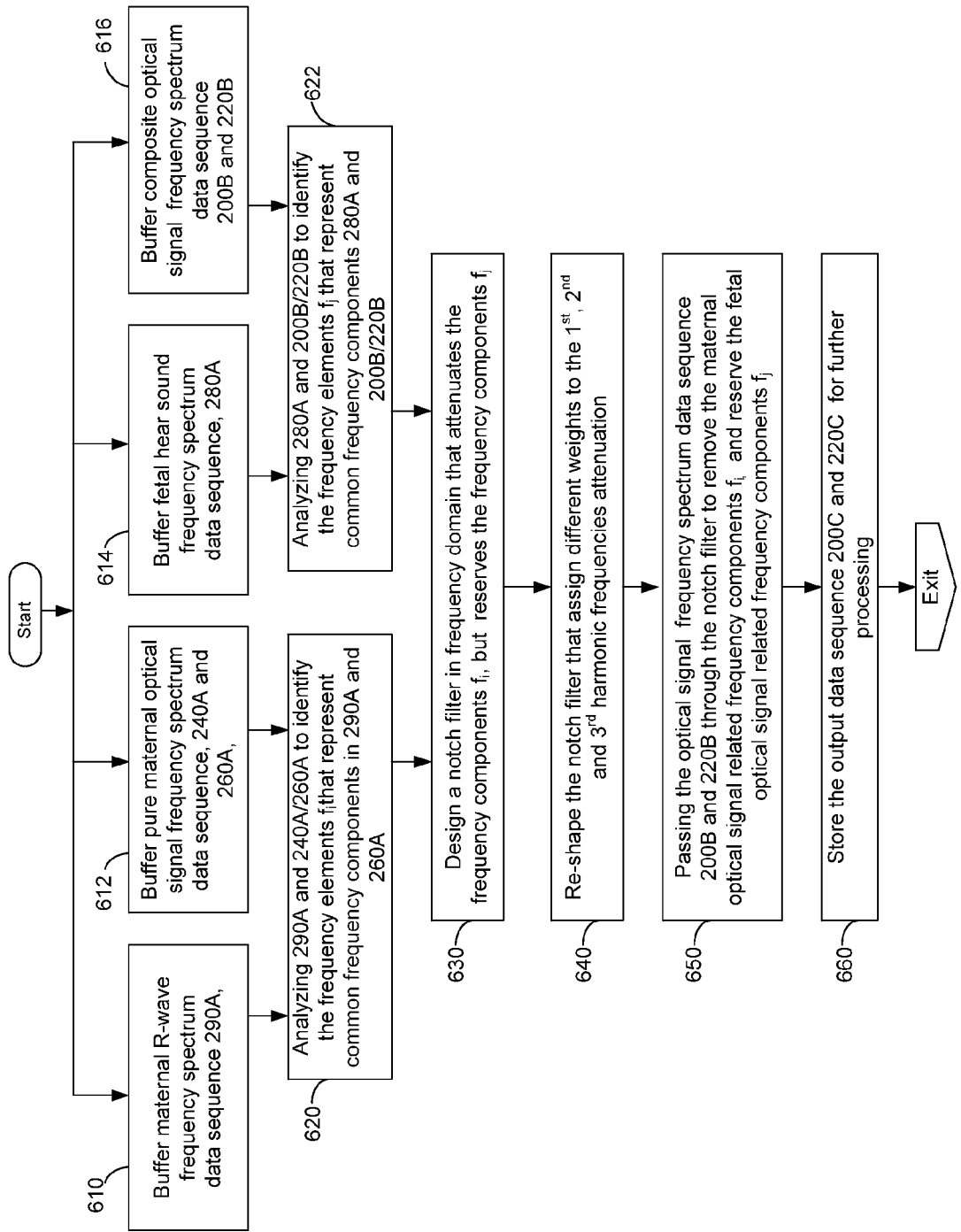

Fig. 11

$$x(t_n) = \frac{1}{N} \sum_{k=0}^{N-1} X(\omega_k) e^{j\omega_k t_n}, \qquad n = 0, 1, 2, \ldots, N-1.$$

Fig. 11A $$x_n = x[n] = z^{-1}[X(z)] = \frac{1}{2\pi i}\oint_C X(z) z^{n-1} dz$$

METHOD AND APPARATUS FOR NON-INVASIVE FETAL OXIMETRY

BACKGROUND OF THE INVENTION

1. Field of the Invention

The present invention relates generally to methods and devices to monitor patient blood oxygen saturation, and more specifically to methods and devices used to measure the oxygen saturation level of the arterial blood flow of a fetus.

2. Description of the Prior Art

The later stages of pregnancy, as well as labor and delivery, can be a dangerous time for the fetus. If the fetal umbilical cord becomes twisted in an unfavorable position, the placenta detaches prematurely, or if the fetus is otherwise placed in a situation of undue stress, fetal blood oxygen saturation levels can fall dangerously low, resulting in potential fetal brain damage (such as cerebral palsy) or death.

Although fetal heart monitors can be used as a surrogate means to attempt to measure fetal blood oxygen saturation levels, this method is indirect, and thus does not give a fully complete understanding of the fetal status. As a result of this lack of full understanding, emergency medical decisions, such as when to start an emergency caesarean section (C-section) must be made with incomplete knowledge. As a practical matter, doctors tend to err on the side of caution, resulting in many unnecessary C-sections, and the attendant high medical expenses and maternal post-childbirth complications.

Previous attempts to provide this missing fetal blood oxygen saturation levels include the OxiFirst system, produced by Mallinckrodt/Nellcor, now part of Tyco Healthcare. This system, which obtained FDA approval in 2000, works by directly placing the tip of a pulse oximeter sensor up the maternal birth canal, through the cervix, into the uterus and onto the cheek or temple of the fetus. Due to this very invasive insertion process, the method is indicated only after the amniotic membrane has ruptured. This method is described in Levinson et. al., U.S. Pat. No. 5,813,980, and other patents. Unfortunately, due to the high invasiveness and bother of the procedure, the method met with limited medical acceptance in the field, and the manufacturer eventually decided to stop selling the device.

Physicians are highly aware that they will be vulnerable to malpractice lawsuits in the event of potentially preventable fetal neurological damage or death. As a result, armed only with a partial picture of the true physiological status of the fetus, they act very conservatively, and usually elect to do C-sections in the event of any sign of fetal heartbeat issues, even though in most situations, the fetal oxygen levels are still adequate. The problem is now so severe that over 30% of all births are now done by C-section, up from only a few percent only a few decades ago. C-sections cost almost twice as much as vaginal deliveries (now averaging more than $5,000 to $10,000 extra per birth), and there are over four million births per year in the US alone. As a result, each year, many billions of dollars of scarce medical resources are wasted performing unnecessary C-sections that might be better spent saving lives elsewhere.

Thus improved methods for monitoring fetal blood oxygen saturation levels are of high practical utility to the fetus, to the mother, and to society at large.

BRIEF SUMMARY OF THE INVENTION

The invention is a method and apparatus to non-invasively measure fetal blood oxygen saturation levels during pregnancy. Optical sensors capable of producing and detecting multiple wavelengths of tissue penetrating light are placed on the surface of the maternal abdomen, and the light beams are directed to pass through at least a portion of the uterus containing the fetus. The fetal heart rate is monitored by Doppler ultrasound or other method, and the pure maternal optical absorption signal and/or maternal heartbeat are also measured. The optical sensors collect composite optical signals containing both maternal and fetal hemoglobin absorption signals and modulated by their respective pulsatile blood flows. The composite signals processed in the time domain and frequency domain, the maternal pulsatile signal used to extract the maternal contribution to the composite signal, and the fetal pulsatile signal is used to lock onto and extract the fetal contribution to the composite signal, the fetal component of the composite signals monitored at two or more wavelengths and a fetal blood oxygen saturation level is calculated.

In one embodiment, the invention is a fetal blood oxygen saturation monitoring method and device that, unlike unsuccessful prior art approaches, works without the necessity to introduce an invasive probe into the mother's uterus or birth canal and onto the fetus. Rather, the invention's improved monitoring device and method operate outside of the uterus and birth canal altogether, and do not require any probe that comes into direct contact with the fetus.

In one embodiment, the method works by placing suitable sensors on the outside surface (skin) of the mother's abdomen, in a safe, unobtrusive, and inexpensive manner designed to encourage widespread adoption.

At the broadest level, the invention is an improved pulse oximetry device and method in which sensors lock onto the signals generated by the maternal pulse and the fetal pulse, as well as optionally other body movements as well. The invention further uses multiple wavelength light beams, selected based upon their ability to penetrate deeply into tissue, ability to distinguish between the oxy and deoxy spectral characteristics of adult hemoglobin, and optionally to distinguish between the oxy and deoxy forms of the spectral characteristics of fetal hemoglobin. The multiple wavelength light beams are directed to penetrate through various layers of maternal tissue to the fetal tissue. The resulting transmitted (or in some embodiments reflected) time varying optical signals (here usually simply referred to as "optical signals") are then subjected to signal processing in which sensor information from the maternal pulse, and optionally other maternal movements are used to determine and reject those portions of the signal that are maternal in origin.

The sensor information from the fetal pulse, and optionally other fetal movements as well, is used to lock onto those portions of the composite optical signal that are fetal in origin, and differences in the fetal optical signals at the different wavelengths that are due to oxyhemoglobin vs. deoxyhemoglobin are assessed, and used to determine fetal blood oxygen saturation levels. In an optional embodiment, spectral differences between the oxy and deoxy forms of fetal hemoglobin, versus the spectral differences between the oxy and deoxy hemoglobin forms of adult hemoglobin, can be used to enhance accuracy. In other optional embodiments, the presence of abnormal forms of hemoglobin, such as the hemoglobin forms present in genetic diseases such as sickle cell anemia, may be also be detected and compensated for.

BRIEF DESCRIPTION OF THE DRAWINGS

FIG. 1A is a block diagram of an alternative fetal oximetry system with the sensors, here not including a maternal R-wave electrode, are placed on the skin surface of the maternal body.

FIG. 7 shows the mathematic FFT equation that may be used to transform time domain signals to frequency domain signals for the composite optical signals, pure maternal optical signals, the maternal HR signals, and the fetal HR signals, previously shown in FIG. 4.

FIG. 7A shows the mathematic Z-transform equation, also used to transform time domain signals to the frequency domain signals. This may be used for the composite optical signals, pure maternal HR and fetal HR time domain to frequency domain signal conversion previously shown in FIG. 4.

FIG. 8 shows the typical frequency spectra of the maternal heart rate signal, the pure red and IR maternal optical signals, the composite red and IR optical signals, the fetal heart rate signal and the residual red and IR optical signals after the maternal frequency components are removed, as previously shown in FIG. 4.

FIG. 9 is a signal processing flow chart of the frequency domain maternal optical signal eliminator shown in FIG. 4. In this example, both the maternal R-wave data and the pure maternal optical data are used.

FIG. 11 is the mathematic inverse FFT equation that transforms the frequency domain signals to the time domain signals for the optical signal frequency to time domain conversion, previously shown in FIG. 4.

FIG. 11A is the mathematic inverse Z-Transform equation that transforms the frequency domain signals to the time domain signals for the optical signal frequency to time domain conversion, previously shown in FIG. 4.

DETAILED DESCRIPTION OF THE INVENTION

Figure 1:
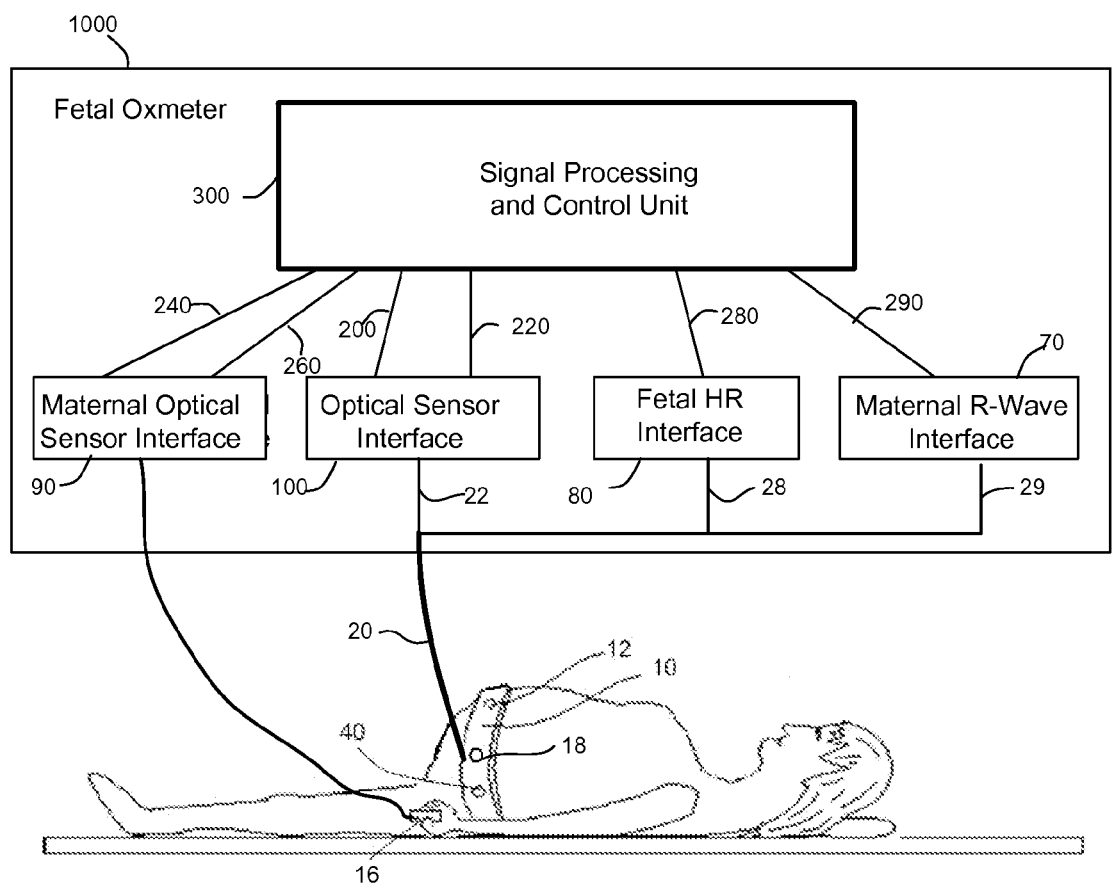
FIG. 1 is a block diagram of the fetal oximetry system where the sensors, here including a maternal R-wave electrode, are placed on the skin surface of the maternal body.

Blood oxygen saturation levels are a critical measure of a patient's well-being. One well known and widely accepted means to measure the oxygen saturation level of blood is oximetry. The light absorption signal of blood hemoglobin differs markedly, as a function of light wavelength, depending upon if hemoglobin is oxygenated or deoxygenated. Thus by monitoring blood light absorption levels at multiple wavelengths, the percentage of the hemoglobin that is bound to oxygen can be estimated to a high degree of accuracy. At red and near infrared wavelengths, the oxygenated form of hemoglobin (oxy-hemoglobin) tends to absorb light more at longer wavelengths, such as 850 nanometers (nm), while the deoxygenated form of hemoglobin (deoxy-hemoglobin) tends to absorb light more at shorter wavelengths, such as 660 nm.

These wavelengths (660 nm and 850 nm) are commonly used for oximetry, and indeed are often used here in this specification as well as examples. However as will be discussed later, for the proposes of this invention, often other considerations will lead away from this common usage, and towards the selection of other wavelengths as well, such as other wavelengths between about 620 nm and 1,200 nm. Indeed sometimes more than two wavelengths may be useful.

Although simple measurements of relative amounts of light absorption at multiple wavelengths are adequate to give accurate amounts of percent oxygen saturation of hemoglobin in vitro (i.e. in a optically precise reaction cell), performing the same measurement in vivo is complicated by the fact that body tissues are often a complex mixture of fat, muscle, bone, collagen, and in the case of pregnancy, amniotic fluid as well. These other tissues also absorb light, and interfere with simple oximetry methods unless ways are found to compensate.

Blood flows through the capillaries and blood vessels of the body in a pulsatile manner, ebbing and flowing with each heartbeat. Thus a difference spectrum between multiple wavelength light passing through a tissue filled with blood during one point of a heartbeat, versus the multiple wavelength light passing through the same tissue, now depleted of blood, during a different point of the heartbeat will tend to subtract out the background spectra due to non-hemoglobin components of body tissues, and thus this difference spectrum can form the basis for a blood oxygen saturation determination on human patients and other creatures of interest.

Thus pulse oximetry works by measuring the pulsatile modulation of two or more different wavelength light beams (light sources) as they pass through a cross section of tissue, such as a finger or other body part. The wavelengths of the two or more light sources are often in the red (R) range, such as 660 nanometers (nm), and in the near infrared (IR) range, such as 850 nm, but may be in other wavelengths as well as the situation dictates. Pulse oximetry has been the subject of a number of prior art patents, exemplified by Larsen, U.S. Pat. No. 5,842,981, and other work. As previously discussed, for simplicity, the two most commonly used wavelengths of 660 and 850 nm will be used for most of the examples in this disclosure, but these specific examples are not intended to be limiting.

For pulse oximetry, the light beams are often produced by light emitting diodes (LED), or other optical light sources, and the light remaining after traversal through the tissue is measured by solid state photo-detectors. Often the LED light sources (or other light sources) and photo-detectors are packaged together as a unitized optical sensor unit.

Pulse oximetry is facilitated by the fact that electrical heart activity, such as the electrical cardiogram (ECG) waveform, in particular R-waves, correlates well with arterial blood pulse flows. Many common forms of pulse oximetry use the physiological activity of the cardiac pulse as a base for the system to determine the oxygen saturation level of blood.

Here, a pulse oximeter may use the cardiac rhythm as a "filter" to determine the relative magnitudes of the AC components of the two absorption waveforms, and to process and calculate the blood oxygen saturation levels.

The detected multiple wavelength optical signals used for pulse oxmetry calculations are periodical pulsatile waveforms that both the signals and information from the pulsatile blood flow, as well as the aperiodic signals and signals unrelated to the pulsatile blood flow.

The periodical pulsatile blood flow waveforms have a very strong correlation to the ECG R-waves. In other words, the multiple wavelength optical signals have the same period as that of the R-wave, as well as the determinable time delay or phase relationship from the R-wave.

In this specification, for simplicity the examples will usually be given using the maternal R-wave as one example of one way to obtain the maternal heart rate, and as one example of information that may be used to subtract the maternal portion of a composite maternal/fetal time-varying optical signal from the composite maternal/fetal time-varying optical signal. However other methods, such as obtaining the maternal heart rate from pure maternal optical signals, or using the sound of the maternal heartbeat (i.e. with a stethoscope like device), pressure oscillations due to the maternal heart beat, ultrasonic imaging and/or Doppler imaging, or any pulse detection device may be potentially used for this purpose. Unless otherwise specified, the term maternal R-wave or ECG-R-wave should be considered to also encompass these alternative methods and devices for obtaining maternal pulse information.

The aperiodic signals are often noise generated by irregular variations in blood flow, including variations caused by muscle movement. These muscle movements may be detected by an optical sensor as spurious pulses that may cause the oximeter to process artifact signals, and in turn generate erroneous data.

By using the relationship of the ECG R-wave and the multiple wavelength optical signals representing the blood flow, the periodic pulsatile waveforms carrying the information encoded in the pulsatile blood flow signal can be enhanced, and the aperiodic signals unrelated to the pulsatile blood flow can be reduced or removed.

One convenient method of performing pulse oximetry calculations is by converting the time varying multiple wavelength optical signals into the frequency domain for frequency domain analysis. This conversion is highly useful, because a frequency domain analysis can utilize the synchronous nature of the heart rate, as well as the asynchronous nature of the noise and motion artifacts, to enhance the signals and reduce noise.

In the frequency domain, the optical signals for a given wavelength that correspond to the pulsatile blood flow have known frequency components. These components include the zero frequency components at the background light intensity level, a fundamental frequency at the frequency of the heart rate, and additional harmonic frequencies that occurs at a multiple of the fundamental frequency.

By contrast, the noise and motion artifacts generated by aperiodical signals (in the optical signal and time domain) have frequencies that spread across the entire spectrum. For example, the background light intensity has frequencies that spread out between the zero frequency and the fundamental frequency. By taking advantage of these known characteristics of the optical signals, we can further remove much of the unwanted background signal. In particular, the maternal frequency component of the optical signal, detected by the optical sensor placed on the skin surface of the maternal abdomen, can be removed. Further, the signal components related to fetal blood flow in the frequency domain can be enhanced.

Accordingly, in some embodiments of the invention, optical sensors capable of generating and detecting optical light beams at two or more optical wavelengths are placed on the skin surface of the maternal abdomen. The maternal heartbeat signal is detected using standard techniques, and the fetal pulse signal is also detected, often by using non-invasive pulse monitoring methods such as Doppler ultrasound fetal heartbeat monitors.

The composite optical absorption signals from the multiple wavelength optical sensors placed on the skin surface of the maternal abdomen will generally comprise three types of signals. These are 1) the periodic pulsatile signals correlated to the maternal cardiac cycle (ECG R-waves, for example); 2) the periodic pulsatile signals correlated to the fetal cardiac cycle, (which can be obtained by a Doppler heartbeat signal, or by other methods); and 3) the aperiodic signals that are considered to be noises generated by irregular variations in the maternal and fetal blood flow. These aperodic signals include, but are not limited to, motion artifacts caused by maternal and fetal muscle movement, as well as fetal movement.

When the invention's optical sensor is placed on the skin surface of the maternal abdomen, the periodic pulsatile signals that correlate to the maternal cardiac cycle are typically much stronger than the periodic pulsatile signals that correlate to the fetal cardiac cycle. In fact, the periodic pulsatile signals correlated to the fetal cardiac cycle are usually small when compared to the aperiodic noise signals as well, and thus good background signal processing methods are usually quite important.

As used herein, composite optical signal refers to the optical absorption signal collected from the optical sensors, here generally assumed to be placed on the skin surface of a maternal abdomen, but which may also be located in alternate positions where fetal tissue may be observed, as situations warrant. The pure maternal optical signal refers to the optical absorption signal collected from the optical sensors placed on any part of the maternal body that will not have any corresponding fetal signal. A maternal finger is often used as an example in this disclosure, but this specific example is not intended to be limiting. The fetal optical signal refers to the optical absorption signal that represents the fetal blood flow, after the maternal optical signal is removed from the optical signal by signal processing.

In one embodiment of the invention, the pure maternal oximetry optical signals (usually collected at multiple wavelengths) and/or the maternal heartbeat signal, the fetal heart rate signal, along with the multiple wavelength composite optical signals detected by the optical sensor placed on the skin surface of the maternal abdomen, are analyzed in the time domain and frequency domain to extract the fetal multiple wavelength oximetry optical signals.

By using time domain signal processing techniques, the periodical pulsatile maternal blood flow signal can be subtracted from the composite optical signals. Further, the time measurements of the pure maternal multiple wavelength optical signals and/or the maternal heartbeat signal, the fetal heart rate signal, and the multiple wavelength composite optical signals can be transformed to frequency domain or Z-domain by Fast Fourier Transform (FFT) or Zed-transform (Z-transform). Then in the frequency domain, the fundamental frequency component and its harmonic frequencies related to the maternal blood flow can be further reduced from the frequency spectrum of the composite optical signal. The fundamental frequency component and its harmonic frequencies related to the fetal blood flow can be used to enhance the frequency components in the optical signal related to the fetal heart rate. Since the noises, motion artifacts and spurious signals have frequencies that are spread throughout the entire frequency spectrum, the frequency intensity of these artifacts and spurious signals can be reduced.

After the maternal blood flow related optical signals and noise, motion artifact and spurious signals are removed or reduced from the composite optical signals, the frequency domain optical spectrum can be converted back to time domain signals by inverse FFT or inverse Z-transform. At the time domain, the periodic characteristics of the fetal heartbeat signal (which again can be obtained by Doppler sensor monitoring or other method), and the correlation between the fetal heartbeat signal and the optical signals, can be used to further enhance the remaining periodic pulsatile signal that is related to the fetal heartbeat.

Thus in one embodiment, the invention may be a method of non-invasively determining fetal blood oxygen saturation levels, comprising sending a plurality of tissue penetrating light beams from a plurality of different wavelength optical light sources through a portion of the maternal body and a portion of the fetus, and detecting the resulting absorbed or reflected light beams, thus obtaining composite time varying maternal and time varying fetal optical signal. This method further operates by detecting the fetal heartbeat, and detecting the pure time varying maternal blood flow optical signal and/or maternal heartbeat signal, and using the pure time varying maternal blood flow optical signal and/or maternal heartbeat signal to reduce the maternal portion of the composite time varying maternal and time varying fetal optical signal. This method further uses the fetal heartbeat to detect and enhance said time varying fetal optical signal related to fetal blood flow, and it also uses the time varying fetal optical signal related to fetal blood flow to compute a fetal blood oxygen saturation level.

In an alternative embodiment, the invention may be a pulse oximeter device for non-invasively determining fetal blood oxygen saturation levels, comprising a plurality of optical light sources capable of producing a plurality of tissue penetrating light beams at a plurality of different wavelengths, at least one photodetector capable of detecting this plurality of tissue penetrating light beams after said light beams pass through tissue. Here the plurality of optical light sources and at the least one photodetector are positioned so as to send light beams through portions of both the maternal body and a portion of the body of a fetus, thus producing a set of composite maternal and fetal optical signal data. This device will further comprise at least one fetal heartbeat sensor producing fetal heartbeat data, at least one maternal optical sensor producing a pure maternal optical signal related to maternal arterial blood flow, and/or a maternal heartbeat sensor producing maternal heartbeat data. Here this maternal optical sensor will generally be placed on a portion of the maternal body that does not intersect the fetus. The device will also comprise at least one processor capable of taking the composite maternal and fetal optical signal, the fetal heartbeat data, the pure maternal optical signal and/or maternal heartbeat data, processing this data in the time domain and frequency domain, reducing the maternal contribution to this composite maternal and fetal optical signal, enhancing the pulsatile optical signal related to fetal arterial blood flow. The at least one processor will then calculate a fetal blood oxygen saturation value from this enhanced fetal optical signal.

Referring to FIG. 1, one embodiment of the present invention relates to a fetal oximeter (1000) with sensors (12), (40), (16), and (18) placed on the body surface of the pregnant woman. The sensors include, but are not limited to the optical sensor (40) that collects the composite optical absorption or reflection signals related to both maternal and fetal blood flows, the fetal heartbeat sensor (12) that detects the fetal heartbeat signal, an optical finger probe sensor (16) to detect the pure maternal optical signal, and electrode (18) for maternal R-wave detection. Note that although in this example, the pure maternal optical signal is shown as being obtained by an optical finger probe sensor (16), other body locations, such as the earlobe, where a good maternal blood flow optical signal may be obtained without any contamination from the fetal signal, may also be used. Indeed, as long as the pure maternal optical signal sensor is placed in an orientation or position where the maternal signal is not subject to interference from the fetal signal, the pure maternal optical signal sensor (16) can even be obtained by or near the composite maternal-fetal optical sensor (40). Thus in some embodiments, both sensor (16) and (40) may be located on a belt (10).

In one embodiment, the optical sensor (40), fetal heart sound sensor (12) and the maternal electrodes (18) are mounted on a belt (10) that can be worn or otherwise placed or affixed on the maternal abdomen. The sensor cable (20) generally comprises of multiple electrical wires sending the sensor signals to the oximeter (1000), although in alternative configurations, sensor cable (20) may be replaced by one or more optical cables or even high-bandwidth, short-range, wireless or infrared communications devices.

In one embodiment, oximeter (1000) comprises a maternal R-wave detector interface (70), a fetal heart rate detector interface (80), a pure maternal optical signal interface (90), a composite optical signal interface (100) and a signal processing and control unit (300).

The maternal R-wave interface (70) can be, but is not limited to, an electronic circuit that detects the maternal R-wave of the maternal ECG from electrode (18) connected through electrical wire (29) via sensor cable (20). The R-wave interface (70) sends the maternal R-wave signal (290) to the signal processing and control unit (300) for processing. The fetal heart rate interface (80) can be, but is not limited to, a Doppler ultrasound fetal heart sound monitoring circuit that can detect the fetal heartbeat motion and/or sound and convert this heartbeat signal to a heart rate signal (280) for the signal processing and control unit (300) to process.

The Doppler ultrasound probe (12) (or other fetal heartbeat detector) is connected to fetal heart rate interface (70) by sensor cable (20) and electrical wires (28). The maternal optical sensor interface (90) controls and receives the optical signals from the maternal optical probe (16), which may be worn, for example, on the maternal finger. The maternal optical sensor interface (90) receives the pure maternal optical signal via the maternal optical sensor cable (24) and sends the AC components of the various wavelength optical signals to control unit (300) for processing. In this example, the pure maternal red optical signal (240) and pure maternal infrared (IR) optical signal (260) are being sent to the signal processing and control unit (300).

The optical sensor interface (100) controls and receives the composite optical signals from the optical sensors (18), mounted on the belt (10), via sensor cable (20) and wire (22). The optical sensor interface (100) processes the composite optical signal (22) and then sends the AC components of the (in this example) composite red optical signal (200) and composite IR optical signal (220) to the signal processing and control unit (300) for processing.

The signal processing and control unit (300) can be a computer, microprocessor system or digital signal processing system. This unit (300) is responsible for the analysis and processing of the received signals, including but not limited to (in this example) the composite red optical signal (200), composite IR optical signal (220), pure maternal red optical signal (240), pure maternal IR optical signal (260), fetal heart rate signal (280) and maternal heart rate signal (290). The signal processing and control unit (300) can also be used to calculate the fetal blood oxygen saturation levels, to store the data, and display the fetal blood oxygen saturation value. The signal processing and control unit (300) is also responsible to control the transmit timing and power of the optical sensor (40) and (16). Since the control unit effectively computes both the maternal blood oxygen saturation levels and the fetal blood oxygen saturation levels, if desired, both levels may be displayed, although human factors analysis should be done to in order to configure a dual display so as to prevent confusion.

FIG. 1A shows another embodiment of the present invention that operates without a maternal R-wave detector. Here the fetal oximeter (1000) has sensors (12), (40) and (16) placed on the body surface of the pregnant woman. However in this embodiment, various maternal R-wave related components previously shown in FIG. 1 (such as the electrode (18) for maternal R-wave detection, electrical wire (29), sensor cable (20), as well as the R-wave interface (70) that sends the maternal R-wave signal (290)) are no longer needed because the maternal heartbeat signal instead can be obtained from the pure maternal optical signal. Otherwise, all other descriptions are the same as previously discussed for FIG. 1.

Figure 2:
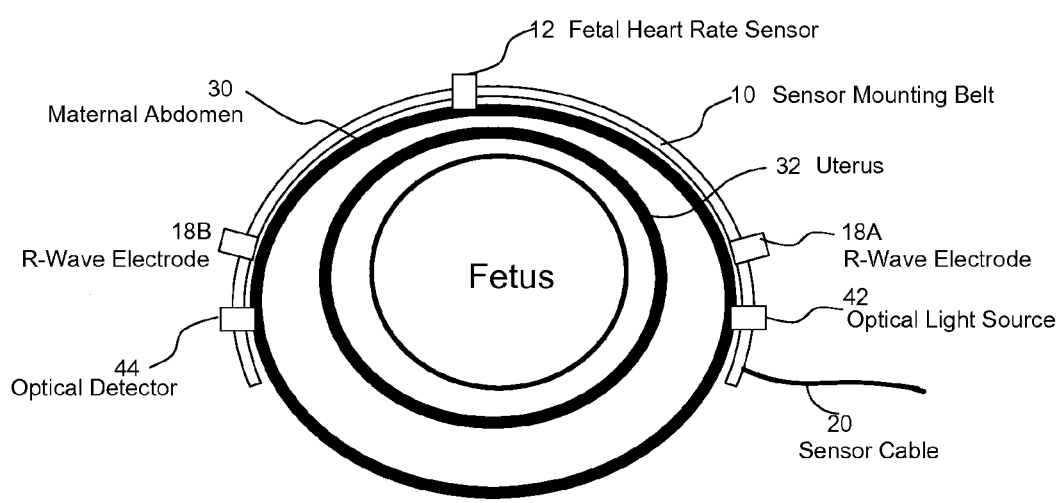
FIG. 2 is a cross-section view of the optical sensors. Here the fetal heartbeat sensor and the maternal ECG R-wave electrodes (or other type of maternal optical blood sensor) are mounted on a belt that is worn on the maternal abdomen.

FIG. 2 shows a cross-section view of the optical light source (42), optical light detector (44), maternal electrodes (18A) and (18B), and fetal heart beat sensor (12), again mounted on a maternal abdomen belt (10) that may be worn on the maternal abdomen (30).

This optical light source (42) is a component of the FIG. 1 optical sensor (40). In principle it may contain a plurality of light sources emitting light at a plurality of wavelengths. In this example, for simplicity, it comprises two light sources, red and infrared LEDs. The optical light detector (44) often consists of photo diodes as well as supporting amplifiers and noise suppression circuitry, which may optionally be tuned for sensitivity at particular wavelength as desired (for example by optical filters). For simplicity, Light Emitting Diodes (LEDs) will be used throughout this application as one example of a suitable type of light source, however this use is not intended to be limiting. In other embodiments, light sources including, but not limited to, lasers, photo emitters, laser diodes, etc. may also be used.

Although FIG. 2 shows the light source (42) and light detector 44 mounted on the opposite locations of the maternal abdomen, in practice the high amount of light attenuation caused by light travel through long tissue distances will generally dictate that light source (42) and light detector (44) be mounted on the same side of the maternal abdomen. Often it will be useful to either employ multiple light sources (42) and detectors (44) and automatically or manually select the most optimal set for getting the strongest fetal signal, or alternatively the light source (42) and light detector (44) can be movable and slid into an optimal position on sensor belt (10).

The maternal R-wave electrodes (18) in FIG. 1 in turn often comprise at least two electrodes (18A) and (18B) that may be mounted on the opposite sides of the maternal abdomen. Although FIG. 2 shows two maternal R-wave electrodes (18A) and (18B), in alternative embodiments, such as the embodiment described in FIG. 1A, (18A) and (18B) are not required because the maternal heartbeat signal can also be obtained from the pure maternal optical signal.

In FIG. 2, the fetal heart beat sensor (12) may be, but is not limited to, an ultrasound transducer such as a Doppler sensor, a fetal stethoscope (fetoscope), or other device. In the preferred embodiment of the present invention, the fetal heart beat sensor (12) can be moved or slid along the sensor belt (10) in order to pick up the strongest fetal heart sound signals.

Figure 3:
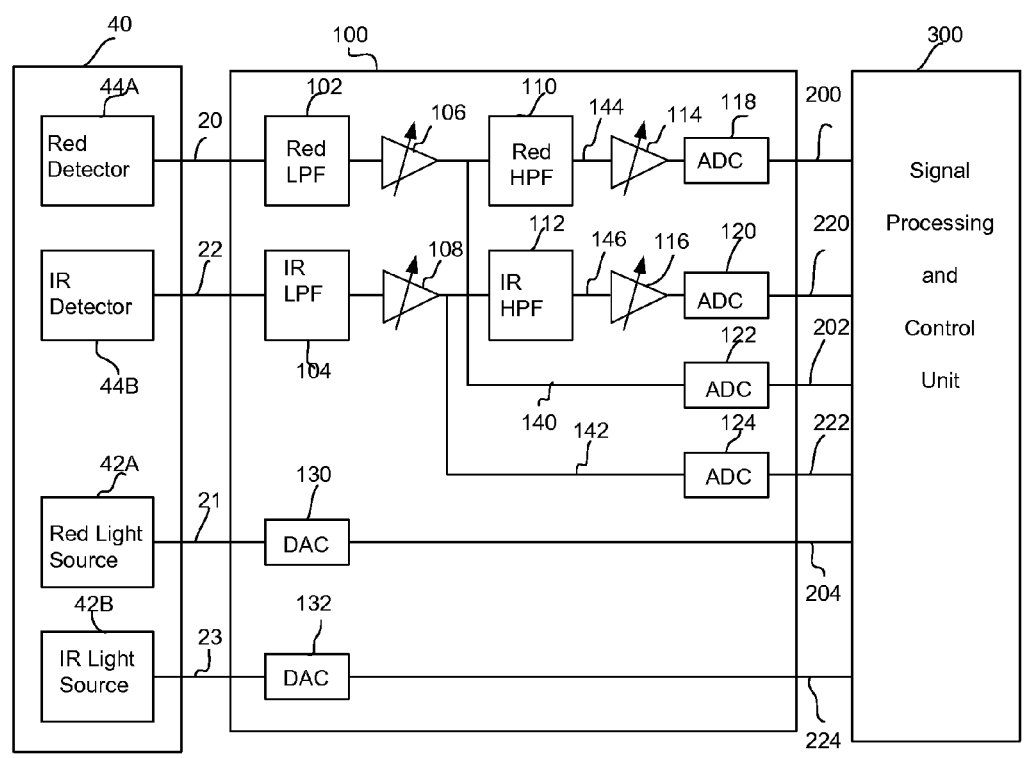
FIG. 3 is a functional block diagram of one embodiment of the optical interface of the fetal oximeter.

Referring to FIG. 3, one embodiment of the optical interface (100) is shown. The optical sensor (40) in turn typically comprises a plurality of light sources operating at different wavelengths. Here again, the red and IR light sources are used as examples. Here red light source (42A) generates red light, IR light source (42B) generates IR light, the red light detector (44A) detects the red absorption signal (20), and the IR light detector (44A) detects the IR absorption signal (22). The high frequency noise of the red signal (20) is often filtered by the low pass filter (102) before it is amplified by the Automatic Gain Control (AGC) amplifier (106). The amplified red signal (140) is then digitized by the Analog to Digital Converter (ADC) (122) and the digitized red signal (202) is received by signal processing and control unit (300).

In the same process, the high frequency noise of the IR signal (22) is filtered by the low pass filer (104) before it is amplified by the AGC amplifier (108). The amplified IR signal (142) is then digitized by the ADC (124) and the digitized IR signal (222) is received by signal processing and control unit (300).

Based on the amplitudes of red signal (202) and IR signal (222), the signal processing and control unit (300) adjusts the transmit power of red light source (42A) and IR light source (42B) so that the amplitudes of red signal (202) and IR signal (222) are within the pre-determined range. To adjust the transmit power of red light source (42A), the signal processing and control unit (300) sends out a power signal (204) that is converted to an analog signal (21) by the Digital to Analog Converter (DAC) (130). To adjust the transmit power of IR light source (42B), the signal processing and control unit (300) sends out a power signal (224) that is converted to an analog signal (23) by the DAC (132).

At the same time, the DC and low frequency components of the amplified red signal (140) are filtered by high pass filter (110) to generate the red AC signal (144) that is amplified by the AGC amplifier (114) before it is digitized by ADC (118). The output signal of ADC (118) is the red optical signal (200) that is sent to the signal processing and control unit (300) for analyzing and processing. In the same way, the DC and low frequency component of the amplified IR signal (142) is filtered by high pass filter (112) to generate the IR AC signal (146) that is amplified by the AGC amplifier (116) before it is digitized by ADC (120). The output signal of ADC (120) is the IR optical signal (220) that is sent to the signal processing and control unit (300) for analyzing and processing.

Figure 4:
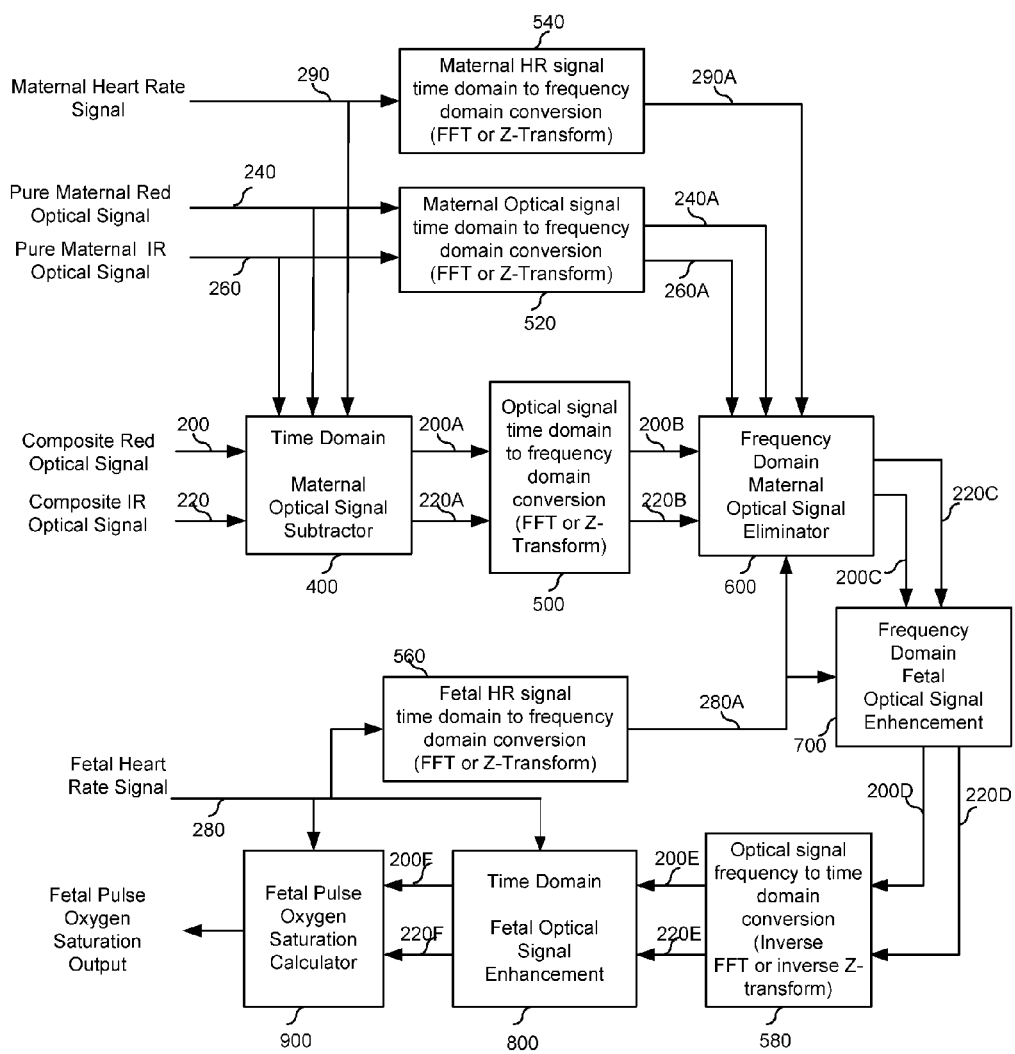
FIG. 4 is a flow chart that shows details of the various signal processing steps performed by the fetal oximeter's digital signal processing and control unit.

FIG. 4 is a flow chart that shows details of the various signal processing steps performed by the fetal oximeter's digital signal processing and control unit (300). This particular signal processing flow starts with subtracting the pure red maternal optical signal (240) and the pure IR maternal optical signal (260) from the composite red optical signal (200) and the composite IR optical signal (220). This is done with (or without) the help of the maternal heart rate signal (290) in time domain, using at time domain maternal optical signal subtractor (400).

The time measurements of the composite Red optical signal (200), composite IR optical signal (220), pure red maternal optical signal (240), pure IR maternal optical signal (260), maternal heart signal (290) and fetal heart rate signal (280) can be Fourier transformed to corresponding frequency domain spectral data sequences, in particular composite red optical spectral data sequence (200B), composite IR optical spectral data sequence (220B), pure red maternal optical spectral data sequence (240A), pure IR maternal spectral optical data sequence (260A), maternal heart rate spectral data sequence (290A) and fetal heart rate spectral data sequence (280A) respectively.

Then the maternal optical signal frequency components can be removed or reduced at frequency domain level by frequency domain maternal signal eliminator (600). After the maternal cardiac related information is removed in both the time domain and the frequency domain, the fetal heart rate frequency data sequence (280A) can be analyzed and used to enhance the fetal heartbeat related frequency components in the red optical spectral data sequence (200C) and the IR optical spectral data sequence (220C) using frequency domain fetal optical signal enhancement (700).

The fetal frequency component enhanced red optical signal (200D) and IR optical signal (220D) are inverse Fourier transformed back to the time domain at (580). In the time domain, the fetal heart rate time measurement (280) is used as a base to further enhance the fetal red optical time measurement of signal (200E) and fetal IR optical time measurement of signal (220E), to generate the fetal blood flow pulsatile information enhanced time measurement of red optical signal (200F) and IR optical signal (220F).

At (900), the enhanced red optical signal (200F) and IR optical signal (220F) are used to determine the fetal pulse oxygen saturation by calculating the ratio of the peaks and valleys at the enhanced time measurement of the red optical signal (200F) and the peaks and valleys at the enhanced time measurement of the IR optical signal (220F).

The detailed descriptions of each of the embodiments and signals in this preferred signal processing flow are given in the following sections.

Although the signal processing flow has been shown and described with reference to this particular signal processing flow in FIG. 4, it will be understood by persons skilled in the relevant art that various changes in forms and details can be made therein without departing from the spirit and scope of this signal processing method. In particular, more than two wavelengths of light may be used. The order of the maternal optical signal removal and the fetal optical signal enhancement in time domain and frequency domain can be altered, or combined in different forms. The signal processing can alternatively be done in the time domain alone or in the frequency domain alone. The fetal oxygen saturation can also be calculated in the frequency domain without being transformed back to the time domain.

Figure 5:
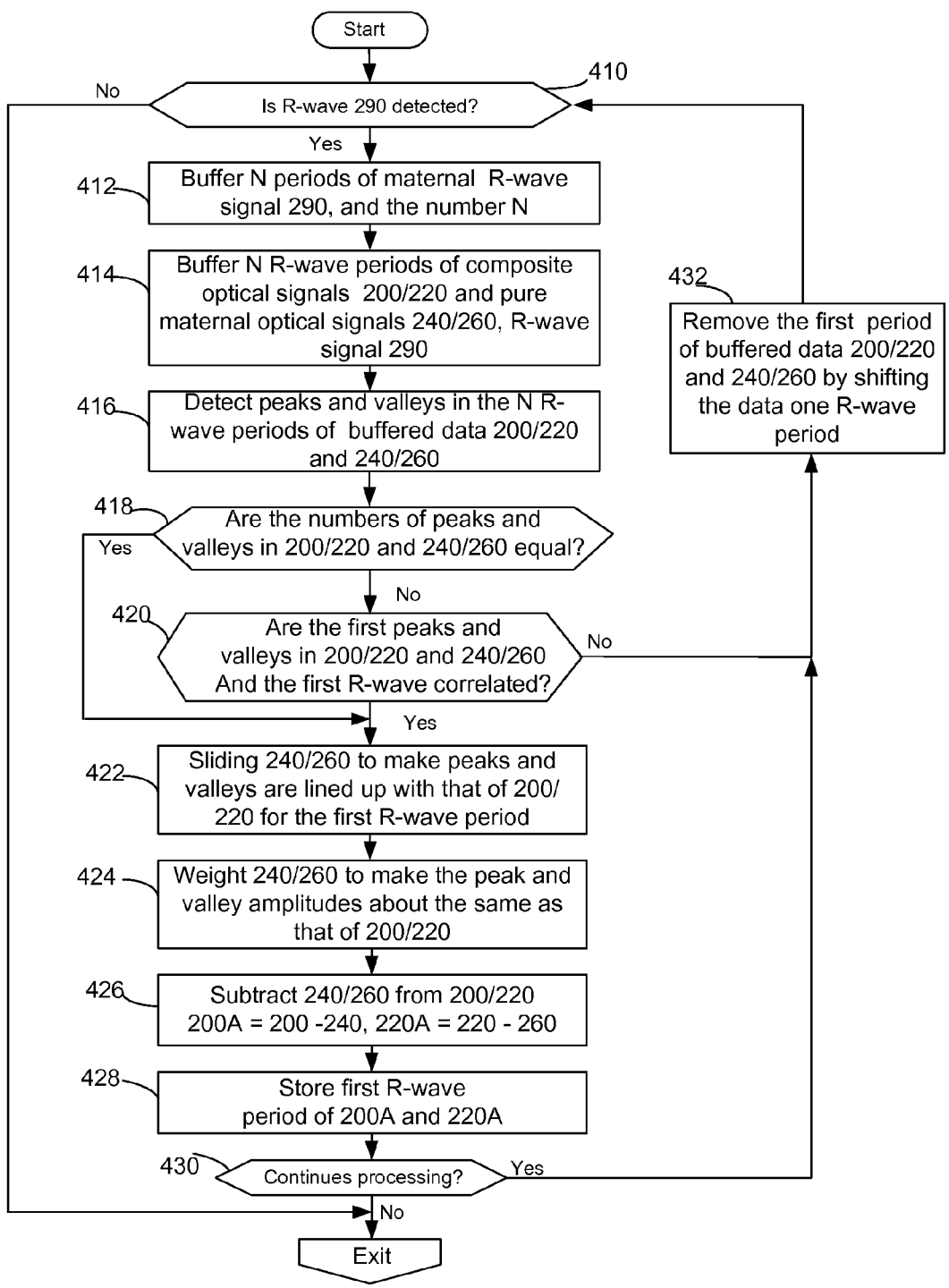
FIG. 5 is a signal processing flow chart of the operations performed by the time domain maternal optical signal subtractor (previously shown in FIG. 4) using, in this example, maternal R-Wave signals to help perform background subtraction.

FIG. 5 is a signal processing flow chart of the operations performed by the time domain maternal optical signal subtractor (400) (previously shown in FIG. 4) using maternal R-wave signals to help perform background subtraction. The process begins with detecting maternal R-wave (290) at (410). If the maternal R-wave (290) is detected, a predetermined number N of R-waves (290) are counted and the number N is stored in a counter. The N cycle time measurements of the maternal R-wave (290) are stored at (412). The same N cycle time measurements of the composite Red optical signal (200), composite IR optical signal (220) and pure red maternal optical signal (240), pure IR maternal optical signal (260) are buffered at (414). Thereafter the peaks and valleys in the buffered data (200/220) and (240/260) are detected at (416). If the number of detected peaks and valleys in the buffered data (200/220) and (240/260) are equal at (418), then the (240/260) data are slid back or forth on the time axis to make the peaks and valleys in the buffered data (200/220) and (240/260) lined up at (422). In other words, the buffered data (240/260) are slid back or forth to make the peaks and valleys in the buffered data (200/220) and (240/260) occur at the same time at (422). Then the buffered data (240/260) are weighted, adjusted, or normalized to make the amplitude from peak to valley of the first R-wave time measurement about the same as the amplitude from peak to valley of buffered data (200/220) at (424). Thereafter the weighted first R-wave time measurements of (240/260) are subtracted from the first R-wave cycle time measurements of (200/220) respectively, to derive red optical signal (200A) and IR optical signal (220A) at (426). Then the first R-wave period of data (200A/220A) are stored at (428). If the process needs to be continued at (430), the first R-wave period time measurements of data in the buffers for (200/220) and (240/260) are removed by sliding the data for the first R-wave period at (432). The process adds another R-wave period time measurement of data at (412), and the next N R-wave period data process then starts.

If the number of detected peaks and valleys in the buffered data (200/220) and (240/260) are not equal at (418), the process checks if the first peaks and valleys in the buffered data (200/220) and (240/260) have the approximate the same time delay from the first maternal R-wave (290) at (420). If the first peaks and valleys in the buffered data (200/220) and (240/260) have cross correlation to the first maternal R-wave (290) at (420), the process continues at (422). If the cross correlation of the first peaks and valleys in the buffered data (200/220) and (240/260) and maternal R-wave (290) can not be found at (420), the first R-wave period of data in the buffers for (200/220) and (240/260) are removed at (432) by sliding the data one R-wave period. In other words, the first R-wave period of buffered data (200/220) and (240/260) are aborted from further processing. The process adds another R-wave period of data, say N+1 period of R-wave, at (412), and the next N R-wave period data process starts.

Figure 5A:
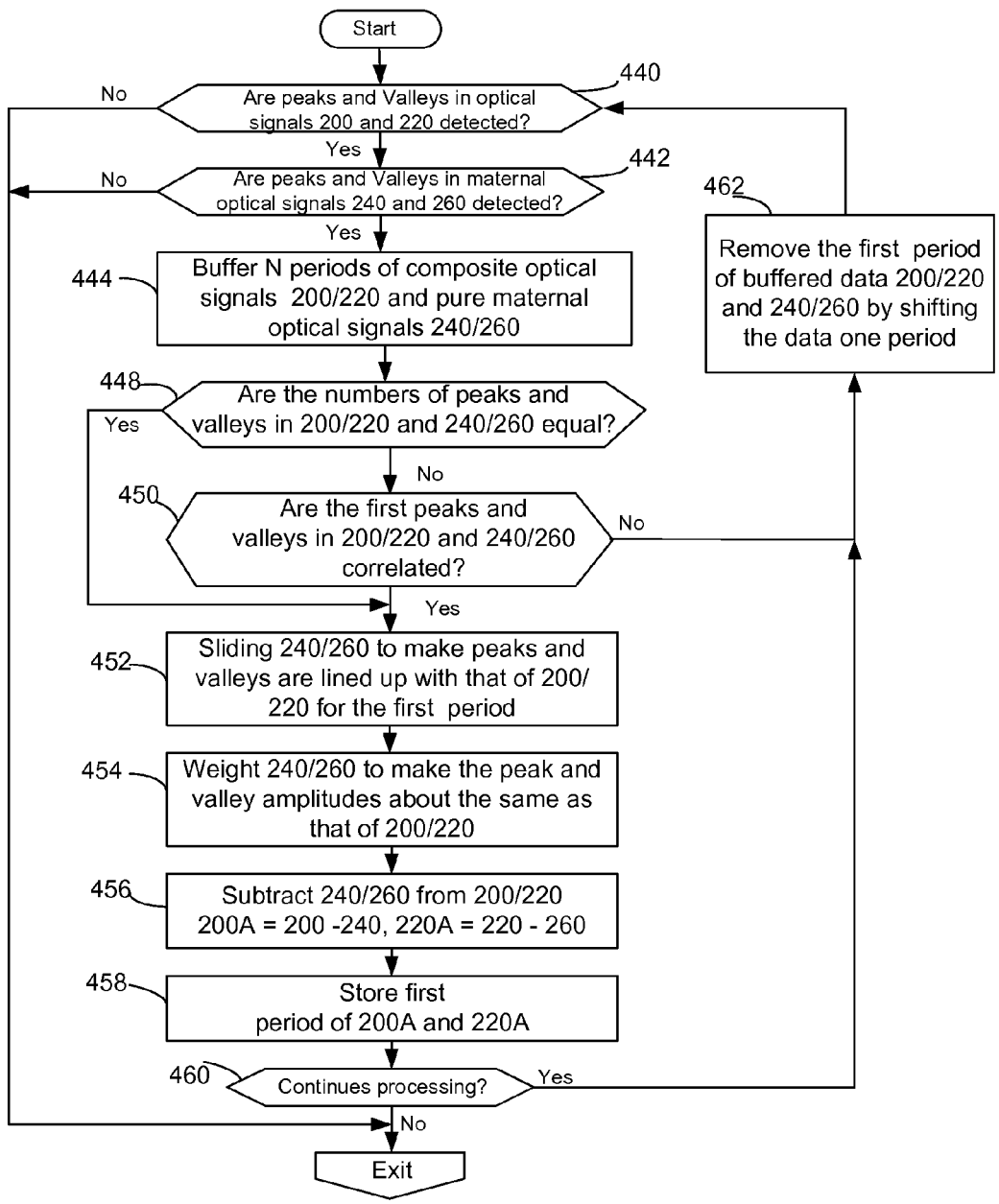
FIG. 5A is a signal processing flow chart of the operations performed by the time domain maternal optical signal subtractor (previously shown in FIG. 4) when, in this example, the maternal R-Wave signal is not used for background subtraction.

FIG. 5A is a signal processing flow chart of the operations performed by the time domain maternal optical signal subtractor (400) (previously shown in FIG. 4) when the maternal R-wave signal is not used for background subtraction. In this flowchart, the maternal R-wave signal (290) is not present. Rather, the process begins with detecting the peak and valleys in the time measurements of the composite Red optical signal (200) and composite IR optical signal (220) at (440). If the peaks and valleys are not found, the process is aborted.

If the peaks and valleys in (200) and (220) are found, then step (442) detects the peaks and valleys in the pure red maternal optical signal (240) and pure IR maternal optical signal (260). If the peaks and valleys in (240) and (260) are not found, the process is aborted.

If the peaks and valleys in (240) and (260) are found, N consecutive peaks and valleys of the time measurements of the composite optical signals (200) and (220) and the pure maternal optical signals (240) and (260) are buffered at (444). If the number of detected peaks and valleys in the buffered data (200/220) and (240/260) are equal at (448), the time measurements of the signals (240/260) are slid back or forth on the time axis to make the peaks and valleys in the buffered data (200/220) and (240/260) line up at (452). In other words, (240/260) are slid back or forth to make the peaks and valleys in the buffered data (200/220) and (240/260) occur at the same time at (452). Then the time measurements of (240/260) are weighted, adjusted, or normalized to make the amplitude from peak to valley of the first R-wave period about the same as that of the peak to valley of (200/220) at (454). Then the weighted (240/260) data are subtracted from (200/220) data respectively for the first peak-to-valley period to derive the red optical signal (200A) and IR optical signal (220A) at (456). Thereafter, the first peak-to-valley period of data (200A/220A) is stored at (458). If the process needs to be continued at (460), the first peak-to-valley period of the time measurement data in the buffers for (200/220) and (240/260) are removed by sliding the data first peak-to-valley period at (462). The process adds another peak-to-valley period of data at (462), and the next N period data process starts.

At (448), if the number of detected peaks and valleys in the buffered (200/220) and (240/260) data are not equal, the first peaks and valleys in the buffered data (200/220) and (240/260) are checked at (450). If the first peaks and valleys in the buffered data (200/220) and (240/260) have cross correlation at (450), the data are further processed at (452). If the cross correlation of the first peaks and valleys in the buffered data (200/220) and (240/260) cannot be found at (450), the first peak-to-valley period of data in the buffers for (200/220) and (240/260) are removed by sliding the data one peak-to-valley period. In other words, the first peak-to-valley period of the buffered data (200/220) and (240/260) are aborted from further processing. The process adds another period of data at (442), and the next N peak-to-valley period data process starts.

Figure 6:
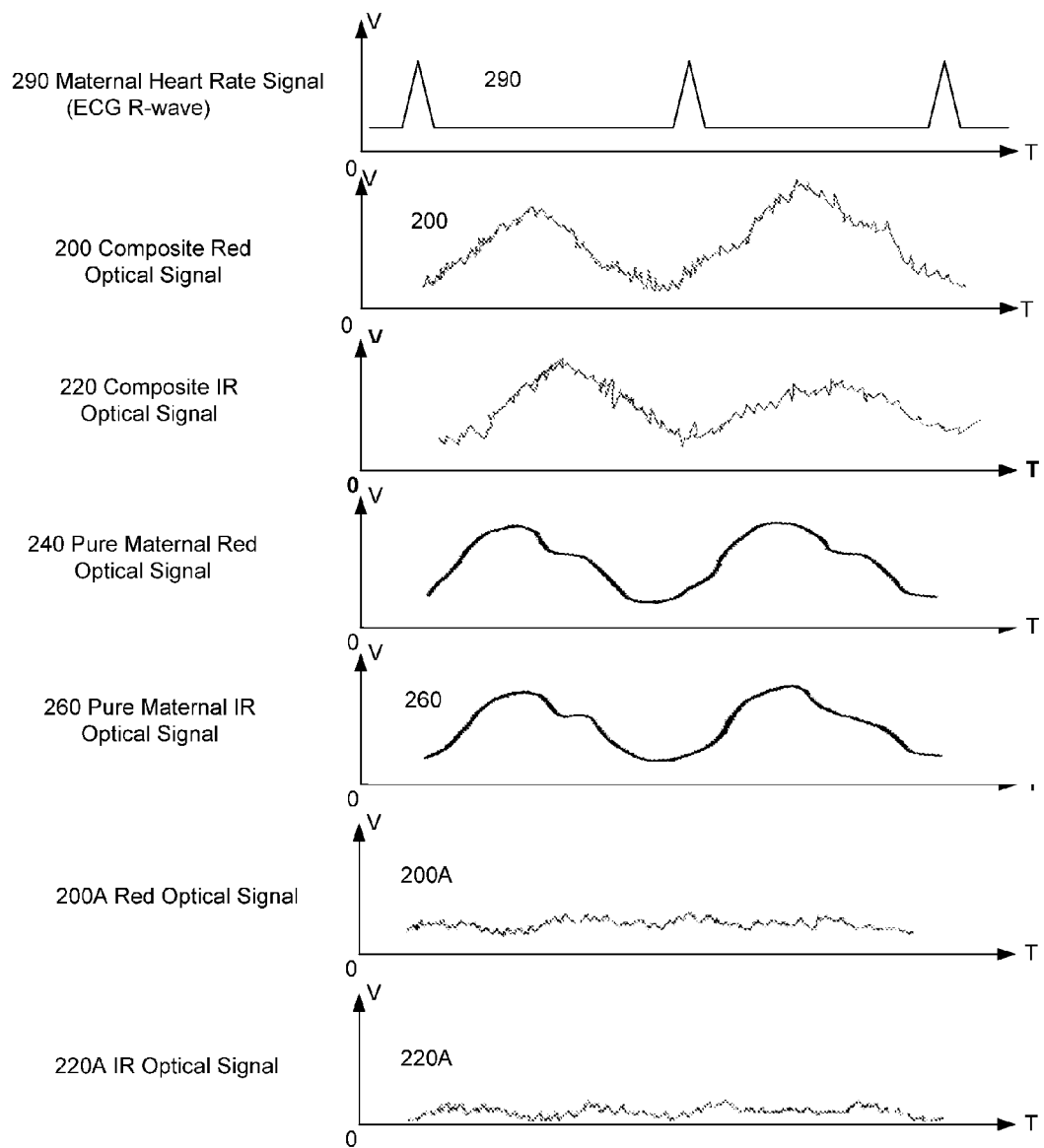
FIG. 6 shows the typical input and output waveforms of the time domain maternal optical signals processed by the FIG. 4 subtractor.

FIG. 6 shows the typical input and output waveforms of the time domain signals processed by the subtractor (400) shown in FIG. 4. Here (290) is an ideal time measurement of the detected waveform of the maternal R-wave. (200) shows a time measurement of waveform of the composite Red optical signal, in which the small red fetal optical signal is superimposed on the large red maternal optical signal plus the noises generated from muscle movements, spurious pulses, fetal movement, etc. Here (220) shows a time measurement of the waveforms of the composite IR optical signal, in which the small IR fetal optical signal is again superimposed on the large IR maternal optical signal and the noise background. (240) shows a time measurement of the waveforms of the pure red maternal optical signal, and (260) shows a time measurement of the waveforms of the pure IR maternal optical signal. The time measurements of signals (200), (220), (240) and (260) generally have similar shape of waveforms, including a plurality of periodic information from successively detected maternal R-waves.

(200A) is the time measurement of the waveform of the red optical signal after the pure red maternal optical signal (240) is subtracted from the composite Red optical signal (200). (220A) is the time measurement of the waveform of the IR optical signal after the pure IR maternal optical signal (260) is subtracted from the composite red optical signal (220).

FIG. 7 shows the mathematic FFT equation that may be used to transform time domain signals to frequency domain signals for the optical signals (200A/220A), pure maternal optical signals (240/260), the maternal HR signals (290), and the fetal HR signals (280), previously shown in FIG. 4. This transform is needed by maternal signal eliminator (600). FIG. 7 shows the FFT equation converting the time-measured red optical signal (200A) and IR optical signal (220A) to red frequency sequence data (200B) and IR frequency sequence data (220B) at the optical signal time to frequency domain conversion (500).

Additionally, the time-measured maternal R-wave signal (290) is converted to the frequency sequence data of the maternal R-wave (290A) at maternal heart rate signal time to frequency domain conversion (540). Further, the pure red maternal optical signal (240) and the pure IR maternal optical signal (260) are converted to pure red maternal frequency sequence data (240A) and pure IR maternal frequency sequence data (260A) at the maternal optical signal time to frequency domain conversion (520). Further, the time-measured fetal heart rate signal (280) is converted to the frequency sequence data of fetal heart rate (280A) at fetal heart rate signal time to frequency domain conversion (560).

In another embodiment of the present invention, the time to frequency domain signal conversion in (500), (520), (540) and (560) can be alternatively be performed using the Z-transform. FIG. 7A gives the mathematic equation of the Z-transform.

FIG. 8 shows the frequency spectrum of the signals being converted to frequency domain. (290A) is the frequency spectrum of the maternal R-wave (290). (240A) is the frequency spectrum of the pure red maternal optical signal (240). (200B) is the frequency spectrum of the red optical signal (200A). (280A) is the frequency spectrum of the fetal heart rate (280). (200C) is the frequency spectrum of the red optical signal (200A) after the pure red maternal frequency components (240A) are removed by the frequency domain maternal optical signal eliminator (600).

FIG. 9 is a signal processing flow chart of the frequency domain maternal optical signal eliminator (600) shown in FIG. 4, here using both maternal R-wave and pure maternal optical spectral data sequences. The processing starts with buffering the frequency spectrum data sequences. The maternal R-wave frequency spectrum data sequence (290A) is buffered at (610). The pure red maternal optical signal frequency spectrum data sequence (240A) and the pure IR maternal optical signal frequency spectrum data sequence (260A) are buffered at (612). The fetal hear sound frequency spectrum data sequence (280A) is buffered at (614). Then the red optical signal frequency spectrum data sequence (200B) and the IR optical signal frequency spectrum data sequence (220B) are buffered at (616).

The buffered maternal heart rate frequency data sequence (290A) has strong fundamental frequency components $f_i$ that are related to the maternal blood flow. The buffered red maternal optical signal frequency data sequence (240A) and the IR maternal optical signal frequency data sequence (260A) also have strong fundamental frequency components $f_i$ that are related to the maternal blood flow. The fundamental frequency components $f_i$ that are related to the maternal blood flow are identified by power spectral density analysis of the buffered sequence data at (620).

By contrast, the buffered fetal heart rate frequency data sequence (280A) has strong fundamental frequency components $f_j$ that are related to the fetal blood flow. The buffered red optical signal frequency data sequence (200B) and the IR maternal optical signal frequency data sequence (220B) also contain frequency components $f_j$ that are related to the fetal blood flow. Here, the fundamental frequency components $f_j$ that are related to the fetal blood flow are identified by power spectral density analysis of the buffered sequence data stream at (622).

Once the fundamental frequency components $f_i$ that are related to the maternal blood flow are identified at (620), and the fundamental frequency components $f_j$ that is related to the fetal blood flow are identified at (622), we can design a frequency domain notch filer that attenuates the frequency components $f_i$ that are related to the maternal blood flow, but on the other hand preserves or reserves the frequency components $f_j$ that are related to the fetal blood flow at (630). The filter (630) also passes the frequencies from the zero frequency to the fundamental frequency $f_i$ of the fetal blood flow.

Since the pure maternal optical signal has been removed by the time domain maternal optical signal subtractor (400), and the fundamental frequency components of the maternal heart rate signal have already been reduced, the notch filter needs to assign different attenuation weights to the fundamental frequency, 2nd and 3rd harmonic frequency components at (640) so that the fetal blood flow related frequency information can be preserved and reserved. Based on how strong the frequency components $f_j$ that are related to the fetal blood flow are identified in the optical data sequence (200B) and (220B), other filter parameters, such as, but not limited to, filter windows, filter coefficients and filter attenuation factors, etc. can be used at step (640) as well.

Next, the buffered red optical signal frequency data sequence (200B) and the IR maternal optical signal frequency data sequence (220B) are passed through the notch filer (640), and are used to generate the red optical signal frequency data sequence (200C) and the IR maternal optical signal frequency data sequence (220C) at (650) by multiplying the sequence data (200B) and (220B) with the filter sequence data in the frequency domain.

As a result, (200C) is the red optical signal frequency domain data sequence after the maternal frequency components relating to the maternal blood flow have been removed. (220C) is the IR optical signal frequency domain data sequence after the maternal frequency components relating to the maternal blood flow have been removed. We then store the red optical signal frequency data sequence (200C) and the IR maternal optical signal frequency data sequence (220C) at (660).

Figure 9A:
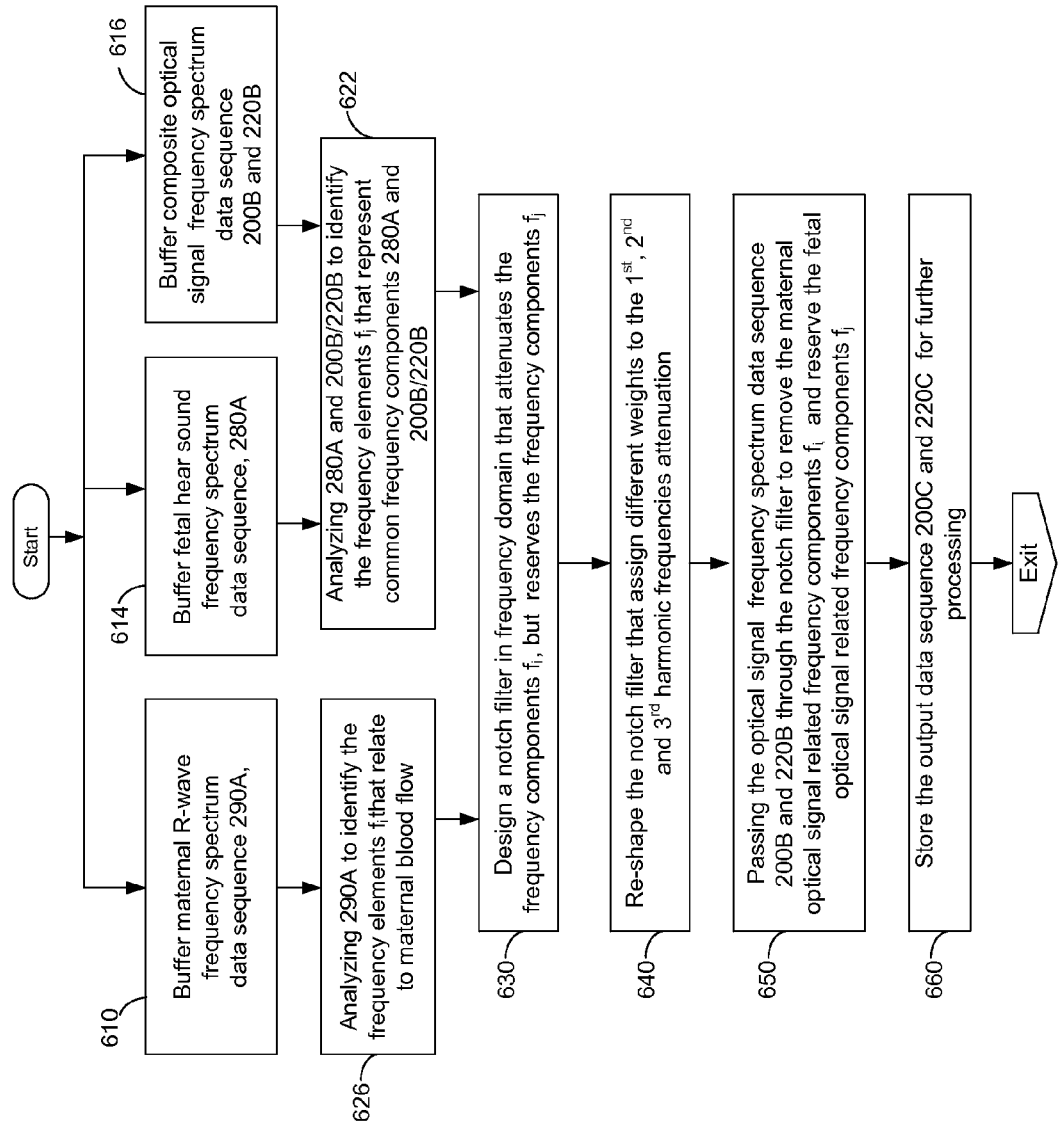
FIG. 9A is a signal processing flow chart of the frequency domain maternal optical signal eliminator shown in FIG. 4. In this example, only the maternal R-wave data is used.

FIG. 9A is a signal processing flow chart of the frequency domain maternal optical signal eliminator (600) shown in FIG. 4 here using only the maternal R-wave spectral data sequences to process the data. The difference between FIG. 9 and FIG. 9A is that in FIG. 9A, the pure maternal red and IR optical signal frequency data sequences (240A) and (260A) are not used to indentify the fundamental frequency components $f_i$ that are related to the maternal blood flow. Instead, the fundamental frequency components $f_j$ related to the maternal blood flow are identified by the maternal heart rate signal frequency data sequence (290A) at (626). Otherwise, the descriptions of all of the other processes in the flow chart FIG. 9A are identical to the previous discussion of FIG. 9.

Figure 9B:
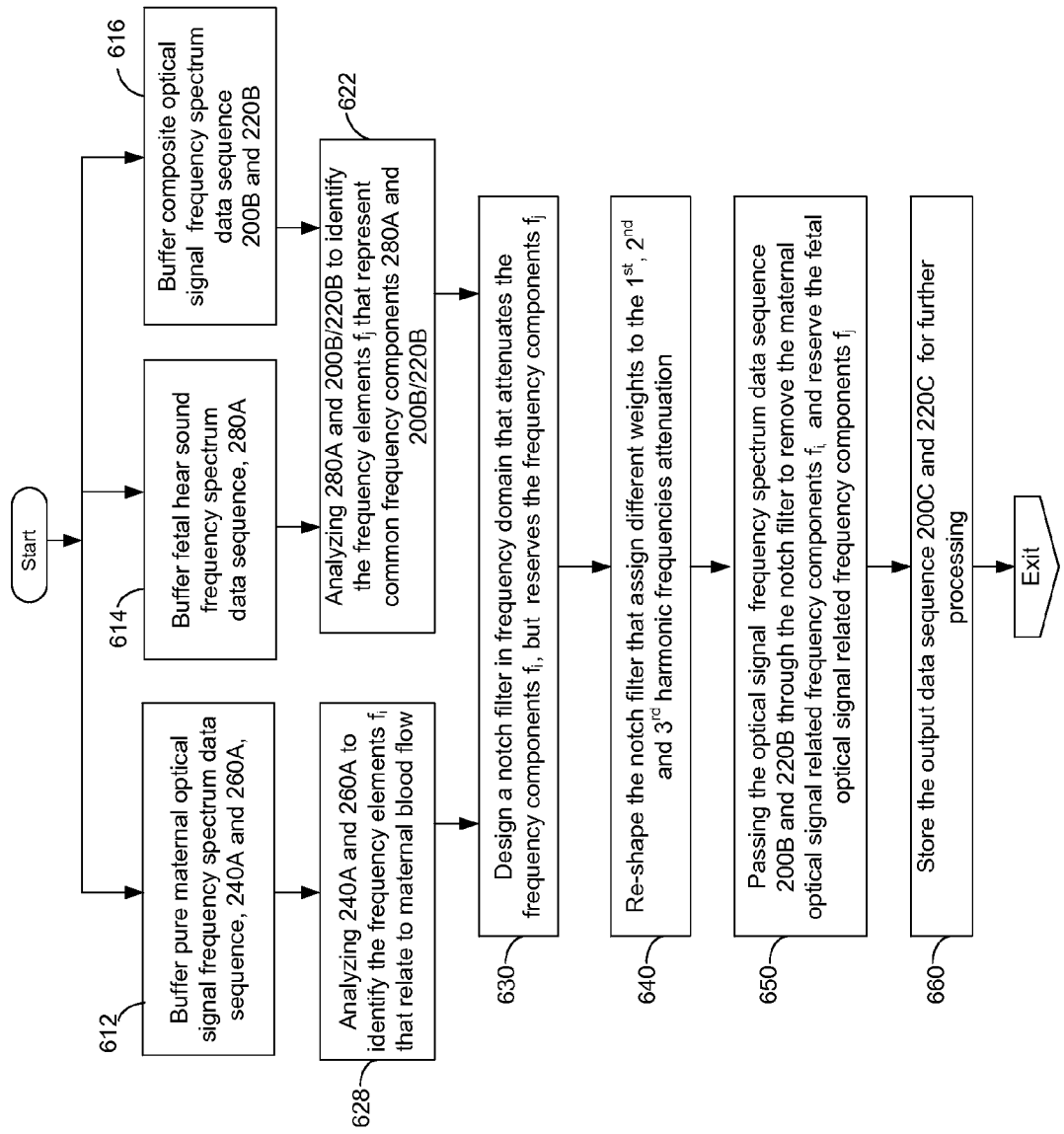
FIG. 9B is a signal processing flow chart of the frequency domain maternal optical signal eliminator shown in FIG. 4, here using only the pure maternal optical data sequences.

FIG. 9B is a signal processing flow chart of the frequency domain maternal optical signal eliminator (600) shown in FIG. 4, here using only the pure maternal optical signal spectral data sequences to process the data. The difference between FIG. 9 and FIG. 9B is that in FIG. 9B, the maternal heart rate signal frequency data sequence (290A) is not used to indentify the fundamental frequency components $f_i$ that are related to the maternal blood flow. Rather, the fundamental frequency components $f_i$ related to the maternal blood flow are instead identified by the pure maternal red and IR optical signal frequency data sequences (240A) and (260A) at (628). Otherwise, the descriptions of all of the other processes in the flow chart FIG. 9B are identical to the previous discussion of FIG. 9.

Referring to FIG. 9, FIG. 9A and FIG. 9B, there can also be other variations of the data processing flowchart of the Frequency-domain Maternal Optical Signal Eliminator (600) previously shown in FIG. 4. For example, to identify the fundamental frequency components $f_j$ that are related to the fetal blood flow at (622), one instead can use only the fetal heart rate frequency data sequence (280A) without using the red optical signal frequency data sequence (200B) and the IR maternal optical signal frequency data sequence (220B).

Figure 10:
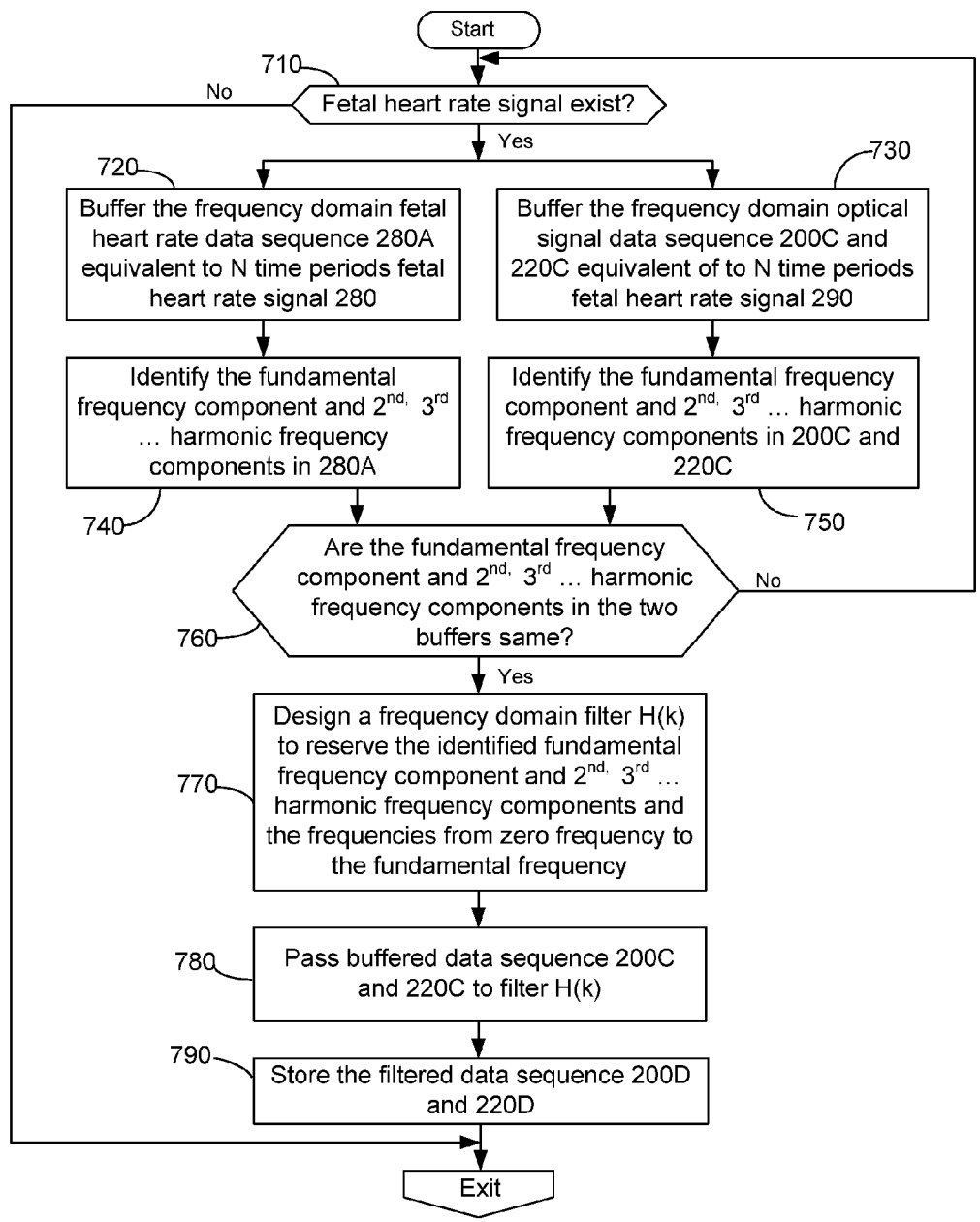
FIG. 10 is a flow chart of the frequency domain fetal signal processing enhancement shown in FIG. 4.

FIG. 10 is a flow chart of the frequency domain fetal signal processing enhancement (700) shown in FIG. 4. The process starts with detecting the fetal heart rate frequency spectrum data sequence (280A) at (710). A picture of this general frequency spectrum of the fetal heart rate (280A) is also shown in FIG. 8. (280A) has its highest amplitudes of the frequency lines at fundamental frequencies relating to the fetal heart beat, and the multiple harmonic frequency lines are tied to this same fundamental frequency. If the fetal heart rate frequency data sequence (280A) is not detected, the process is aborted. If the fetal heart rate frequency data sequence (280A) exists, then the frequency domain fetal heart rate data sequence (280A) is converted from predetermined N time periods of the fetal heart rate signal (290) and is buffered at (720). Additionally, the frequency domain fetal red optical data sequence (200C) and the IR optical data sequence (220C) are converted from the same N time periods and are buffered at (730). The fundamental frequency and its $2^{nd}$, $3^{rd}$ harmonic frequencies of the fetal heart rate data sequence (280A) and fetal optical data sequences (200C) and (220C) are identified at (740) and (750) respectively.

The identified fetal heartbeat fundamental frequency and its $2^{nd}$, $3^{rd}$ harmonic frequencies of fetal heart rate and fetal optical signal are analyzed and compared at (760). If the fetal heartbeat fundamental frequency and the $2^{nd}$, $3^{rd}$ harmonic frequencies of the fetal heart rate and fetal optical signal do not match, the buffered data at (720) and (730) are abandoned, and the processing flow passes to (710) to process next batch of data. If the fetal heart beat fundamental frequency and its $2^{nd}$, $3^{rd}$ harmonic frequencies of fetal heart rate and fetal optical signal match, a frequency domain filter H(k), k=1, 2, ... n, is constructed at (770). Here, the pass band of the filter is the fundamental frequency, and its $2^{nd}$, $3^{rd}$ ... harmonic frequencies previously identified at (720), as well as the frequencies from zero frequency to the fundamental frequency that represent the frequency components of the light background intensity in the fetal optical signal (200C) and (220C). Thereafter, the data sequences (200C) and (220C) buffered at (730) are passed through the filter H(k) at (780) to attenuate the noise frequency components in the fetal optical signal (200C) and (220C) respectively. The output data sequence (200D) is the red fetal optical frequency data sequence, and (220D) is the IR fetal optical frequency data sequence. The data sequences (200D) and (220D) are stored at (790).

Figure 11A:
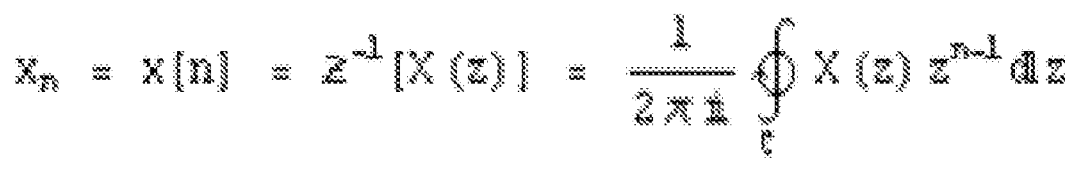

FIG. 11 is the mathematic inverse FFT equation that transforms the frequency domain signals to the time domain signals for the optical signal frequency to time domain conversion (580), previously shown in FIG. 4. Here at (580), the red optical frequency spectral data sequence (200D) and the IR optical frequency spectral data sequence (220D) are taken as input data sequences and are converted back to the time domain red optical signal (200C) and IR optical signal (220C) respectively. By contrast, FIG. 11A gives an alternative inverse Z-transform equation for the frequency to time domain conversion that may be used in an alternative embodiment of the invention. The inverse Z-transform equation is used if the previous frequency domain maternal optical signal eliminator (600) and the frequency domain fetal optical enhancement were previously implemented in the Z-domain.

Figure 12:
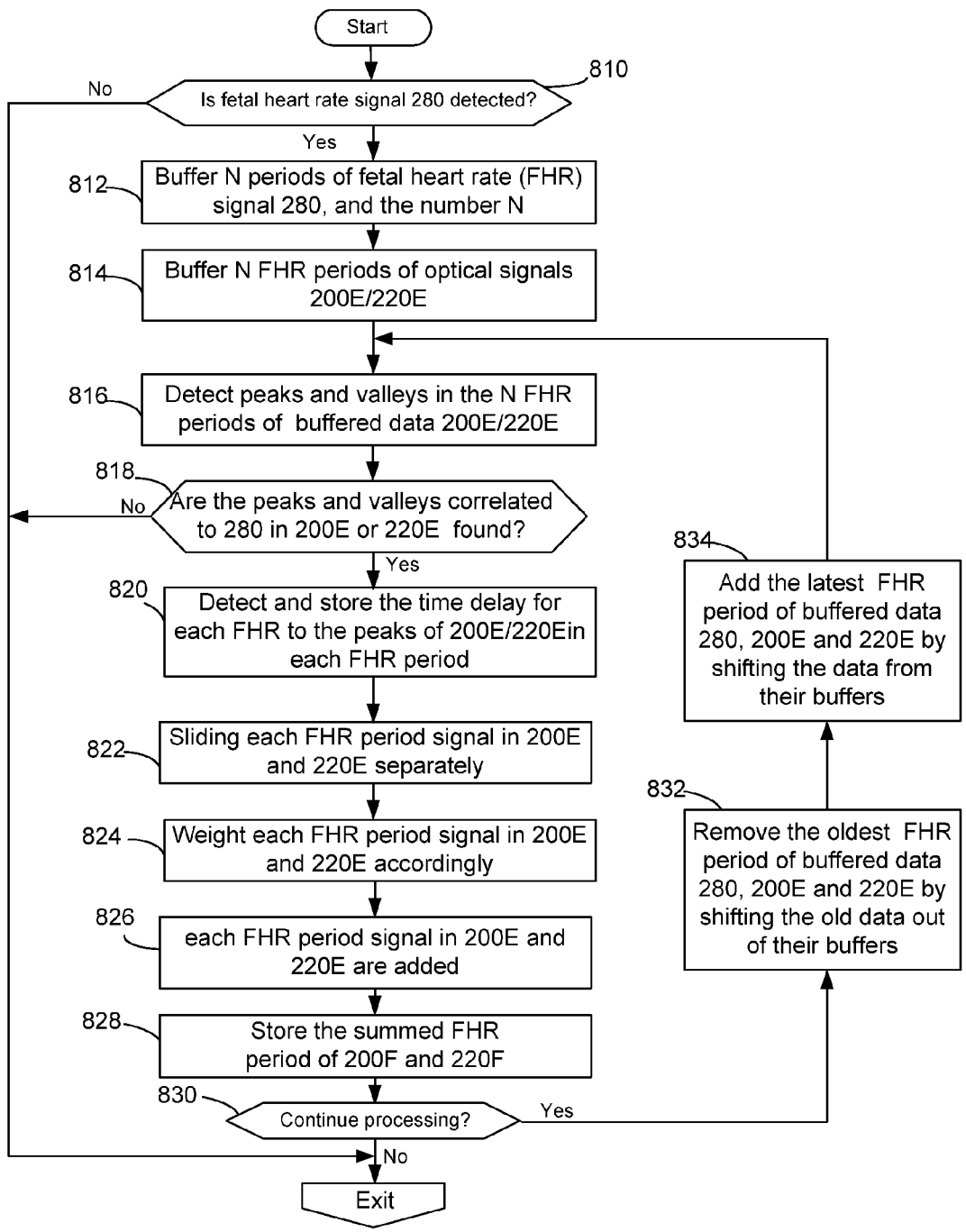
FIG. 12 is a signal processing flow chart for the time domain fetal signal enhancement, previously shown in FIG. 4.

FIG. 12 is a signal processing flow chart for the time domain fetal signal enhancement (800), previously shown in FIG. 4. This process starts with detecting the fetal heart rate signal (FHR) (280) at (810). If the fetal heart rate signal (280) is not detected (810), the process is aborted. If the fetal heart rate signal (280) is detected at (810), pre-determined N periods of the time measurements of the fetal heart rate signal (280) are buffered at (812). Next, the pre-determined N FHR periods of time measurements of the red optical signal (200E) and IR optical signal (220E) are buffered at (814). Thereafter, the peaks and valleys in the buffered N FHR periods of (200E) for the red optical signals and (220E) for IR optical signals are searched and detected at (816). At (818), the correlations of the peaks and valleys of the buffered fetal heart rate signal (280), the buffered red optical signal (200E) and the IR optical signal (220E) are analyzed. If the correlation does not exist, the process is aborted.

If a correlation is found, the time delays for each fetal heart rate (FHR) signal (280) to the peaks of (200E) and (220E) in each FHR period of the buffered FHR, (200E) and (220E) are calculated at (820). For each FHR period, the time measurements of (200E) and (220E) are slid in their time axis so that their the time delay from FHR (280) to peaks of the time measurement of the red optical signal (200E) and the peaks of the time measurement of the IR optical signal (220E) are about the same at (822). Then at (824), each period of the buffered and slid red optical signal time measurement (200E) and IR optical signal time measurement (220E) are weighted (adjusted) so that the newest period of data has the highest weight, and the oldest period of data has the lowest weight. Thereafter, the various periods of the slid weighted red optical time measurement data are added together to generate the red optical signal (200F) at (826). Additionally, each period of the slid weighted IR optical time measurement data are also added together to generate the red optical signal (220F) at (826). Then the signal (200F) and (220F) are stored at (828) for calculation of the fetal pulse oxygen saturation.

If the process needs to be further continued at (830), the oldest FHR period of the buffered FHR (280), the red optical signal (200E), and the IR optical signal (220E) are removed from the buffers at (832). The newest FHR period of the FHR (280), the red optical signal (200E) and the IR optical signal (220E) are added to the buffers at (834). The next FHR period of signal processing starts at (816).

A number of embodiments of the invention are thus possible.

One embodiment of the invention provides a pulse oximetry system that measures the blood oxygen saturation level of fetus during pregnancy noninvasively, and without making direct optical sensor contact with the fetus.

In one embodiment, the optical sensor may be placed on the maternal abdomen to eliminate any invasive or intrusive procedures.

Another embodiment is a fetal pulse Oximetry system where the fetal blood oxygen saturation is derived from two or more received absorption optical signals obtained from photo-detectors placed on the skin surface of the maternal abdomen.

Another embodiment of the invention is a method of data processing for a fetal pulse oximetry system. This method processes the optical signals that comprise the periodic pulsatile signals related to the pulsatile of the maternal blood flow, the periodic pulsatile signals related to the pulsatile fetal blood flow, and the aperiodical signals that are considered to be noises unrelated to either maternal heart rate or fetal heart rate, and uses these signals to subtract the unwanted maternal background signal from the fetal blood flow signal.

Another embodiment of the invention is a fetal pulse oximetry system that uses one or more optical sensors containing, but not limited to, light emitting diodes and solid state photodetectors. The optical sensors may include, but are not limited to, light sources that emit two or more beams of light at different wavelengths. In one example, two lights may be used with wavelengths in the red (R) range of about 660 nm, and the near infrared (IR) range of about 850 nm.

In other embodiments, optical sensor light sources may be used that emit light at alternate wavelengths (often chosen from the near infrared (IR) region) selected on the one hand to have maximum tissue penetrating distances, and also selected on the other hand to still retain an ability to distinguish between the oxy and deoxy forms of adult and/or fetal hemoglobin.

Another embodiment is a fetal pulse oximetry system that uses maternal heart rate signals, such as ECG R-wave signals, to improve the signal to noise levels of the resulting fetal oximetry data.

Another embodiment is a fetal pulse oximetry system that uses pure maternal optical arterial blood flow absorption signals to improve the signal to noise levels of the resulting fetal oximetry data.

Another embodiment is a fetal pulse oximetry system that utilizes the maternal heart rate, the pure maternal optical signals, and time domain processing to remove or reduce the periodical pulsatile maternal optical signals from the received composite optical signals of the optical detectors placed on the skin surface of the maternal abdomen.

Another embodiment is a fetal pulse oximetry system that utilizes the maternal heart rate and pure maternal optical signals to remove the maternal frequency components from the received composite optical signals of the optical detectors placed on the skin surface of the maternal abdomen, using frequency domain signal processing.

Another embodiment is a fetal pulse oximetry system that utilizes the periodic fetus heart rate signal to extract the periodical pulsatile fetal optical signals from the processed composite optical signals of the optical detectors placed on the skin surface of the maternal abdomen. Here this overall maternal signal is first processed by using the periodic maternal pulsatile optical signal, as well as other aperiodic noise signals, to remove the maternal background (and background originating from fetal and maternal muscle movements) from the composite optical signal.

Another embodiment is a fetal pulse oximetry system where the maternal abdomen optical sensors, the maternal heart sensors and the fetal heart rate sensor(s) are mounted on a belt that can be conveniently and comfortably worn or otherwise positioned on the maternal abdomen.

Although the description has been particularly shown and described with reference to multiple embodiments, it will be understood by persons skilled in the relevant art that various changes in form and details can be made therein without departing from the spirit and scope of the specification.

The invention claimed is:
1. A method of non-invasively determining fetal blood oxygen saturation levels, comprising:
    sending a plurality of tissue penetrating light beams from a plurality of different wavelength optical light sources through a portion of the maternal body and a portion of the fetus, and detecting the resulting transmitted or reflected light beams, thus obtaining composite time varying maternal and time varying fetal optical signals related to maternal and fetal arterial blood flows;
    detecting the fetal heartbeat;
    detecting the pure time varying maternal optical signals related to maternal arterial blood flows and/or maternal heartbeat;
    using said pure time varying maternal optical signals and/or maternal heartbeat to reduce the maternal portion of said composite time varying maternal and time varying fetal optical signal;
    using said fetal heartbeat to detect and enhance said time varying fetal optical signal
    and using said time varying fetal optical signal to compute a fetal blood oxygen saturation level.

2. The method of claim 1, in which said different wavelengths comprise tissue penetrating two or more wavelengths between 620 nm and 1,200 nm.

3. The method of claim 1, wherein said fetal heartbeat is detected using a Doppler ultrasound device, fetal stethoscope, or other method.

4. The method of claim 1, wherein said maternal heartbeat is detected from the pure time varying maternal optical signals related to maternal arterial blood flow, or by maternal ECG R-wave electrodes, or other method.

5. The method of claim 1, wherein at least one light emitting device to produce said plurality of tissue penetrating light beams, and at least one light detecting device to detect said resulting transmitted or reflected light beams are located on a belt or other holder device and placed on the skin of the maternal abdomen.

6. The method of claim 1, wherein said pure time varying maternal blood optical signal is obtained by an optical sensor positioned to pass light beams through a portion of said maternal body that does not intersect the fetus.

7. The method of claim 6, wherein said pure time varying maternal optical signal is obtained by an optical sensor positioned on a maternal finger or other part of said maternal body.

8. The method of claim 1, further transforming said pure time varying maternal optical signal and time varying fetal optical signal into the frequency domain by a first transform;
reducing said maternal portion of said composite time varying maternal and time varying fetal spectral data in said frequency domain;
and detecting and enhancing said time varying fetal spectral data in said frequency domain.

9. The method of claim 8, wherein said first transform is selected from the group consisting of FFT transforms or Z-transforms.

10. The method of claim 1, wherein said time varying fetal spectral data is analyzed for the characteristic optical absorption characteristics of fetal hemoglobin.

11. A method of non-invasively determining fetal blood oxygen saturation levels, comprising:
sending a plurality of tissue penetrating light beams from a plurality of different wavelength optical light sources through a portion of the maternal body and a portion of the fetus, and detecting the resulting transmitted or reflected light beams, thus obtaining composite maternal and fetal optical signals related to maternal and fetal arterial blood flows;
wherein at least one light emitting device to produce said plurality of tissue penetrating light beams, and at least one light detecting device to detect said resulting transmitted or reflected light beams are located on a belt or other holder device and placed on the skin of the maternal abdomen;
detecting the fetal heartbeat using a Doppler ultrasound device, fetal stethoscope, or other method;
detecting pure maternal blood optical data using an optical sensor positioned to pass light beams through a portion of said maternal body that does not intersect the fetus;
detecting the maternal heartbeat from the time varying maternal optical signals related to maternal arterial blood flow, or using maternal ECG R-wave electrodes, or other method;
using said pure maternal blood optical data or said maternal heartbeat data to reduce the maternal portion of said composite maternal and fetal optical signals;
using said fetal heartbeat to detect and enhance the said fetal portion of said composite maternal and fetal optical signals producing an enhanced fetal optical signal;
and using said enhanced fetal optical signal to compute a fetal blood oxygen saturation level.

12. The method of claim 11, further transforming said composite maternal and fetal optical signals into the frequency domain by a first transform producing frequency transformed composite maternal and fetal optical signals;
reducing said maternal portion of said frequency transformed maternal and fetal optical signals in said frequency domain;
and detecting and enhancing said the fetal component of said frequency transformed maternal and fetal optical signals in said frequency domain.

13. The method of claim 12, wherein said first transform is selected from the group consisting of FFT transforms or Z-transforms or other transform method.

14. The method of claim 12, further processing said frequency transformed composite time maternal and fetal optical signals back from the frequency domain into the time domain using an inverse FFT transform or inverse Z-transform or other inverse transform method.

15. A pulse oximeter device for non-invasively determining fetal blood oxygen saturation levels, comprising:
a plurality of optical light sources capable of producing a plurality of tissue penetrating light beams at a plurality of different wavelengths;
at least one photodetector capable of detecting said plurality of tissue penetrating light beams after said light beams pass through tissue;
said plurality of optical light sources and at least one photodetector positioned so as to send light beams through portions of both the maternal body and a portion of the body of a fetus, producing a set of composite maternal and fetal optical signals;
at least one fetal heartbeat sensor producing fetal heartbeat data;
at least one optical sensor producing pure maternal optical data, said maternal optical sensor operating on a portion of said maternal body that does not intersect the fetus;
and/or one maternal heartbeat sensor producing maternal heartbeat data;
at least one processor capable of taking said composite maternal and fetal optical signal data, said pure maternal optical signal data and/or said maternal heartbeat data, processing said data in the time domain and frequency domain, reducing the maternal contribution to said composite maternal and fetal optical signal data, enhancing said fetal optical signal data, and calculating a fetal blood oxygen saturation value from said amplified fetal optical signal data.

16. The device of claim 15, wherein at least some of said plurality of light sources and at least one photodetector are located on a belt or other holder device and placed on the skin of the maternal abdomen.

17. The device of claim 15, wherein at least some of said plurality of light sources, at least one photodetector, said fetal heartbeat sensor, and at least one maternal heartbeat sensor are located on a belt or other holder device and placed on the skin of the maternal abdomen.

18. The device of claim 15, in which said fetal heartbeat sensor is a Doppler ultrasound sensor, fetal stethoscope, or other fetal heartbeat detector.

19. The device of claim 15, in which said maternal heartbeat sensor comprises ECG R-wave electrodes or other heartbeat detector.

* * * * *